United States Patent
Shin et al.

(10) Patent No.: US 6,412,336 B2
(45) Date of Patent: Jul. 2, 2002

(54) SINGLE RISER/SINGLE CAPILLARY BLOOD VISCOMETER USING MASS DETECTION OR COLUMN HEIGHT DETECTION

(75) Inventors: Sehyun Shin, Bryn Mawr, PA (US); Young Cho, Cherry Hill, NJ (US); Kenneth Kensey, Malvern, PA (US); William N. Hogenauer, Gilbertsville, PA (US); Sangho Kim, Philadelphia, PA (US)

(73) Assignee: Rheologics, Inc., Exton, PA (US)

(*) Notice: Subject to any disclaimer, the term of this patent is extended or adjusted under 35 U.S.C. 154(b) by 0 days.

(21) Appl. No.: 09/897,176

(22) Filed: Jul. 2, 2001

Related U.S. Application Data

(63) Continuation-in-part of application No. 09/789,350, filed on Feb. 21, 2001, and a continuation-in-part of application No. 09/573,267, filed on May 18, 2000.
(60) Provisional application No. 60/228,612, filed on Aug. 29, 2000.

(30) Foreign Application Priority Data

Mar. 29, 2000 (KR) .......................................... 2000-16044

(51) Int. Cl.⁷ .............................. G01N 11/06; A01B 5/00
(52) U.S. Cl. ....................................... 73/54.07; 600/573
(58) Field of Search ........................... 723/54.01–54.43; 600/573, 585, 574, 486, 504

(56) References Cited

U.S. PATENT DOCUMENTS

| | | |
|---|---|---|
| 1,810,992 A | 6/1931 | Dallwitz-Wegner |
| 2,343,061 A | 2/1944 | Irany |
| 2,696,734 A | 12/1954 | Brunstrum et al. |
| 2,700,891 A | 2/1955 | Shafer |
| 2,934,944 A | 5/1960 | Eolkin |
| 3,071,961 A | 1/1963 | Heigl et al. |
| 3,116,630 A | 1/1964 | Piros |
| 3,137,161 A | 6/1964 | Lewis et al. |
| 3,138,950 A | 6/1964 | Welty et al. |
| 3,277,694 A | 10/1966 | Cannon et al. |
| 3,286,511 A | 11/1966 | Harkness |
| 3,342,063 A | 9/1967 | Smythe et al. |
| 3,435,665 A | 4/1969 | Tzentis |
| 3,520,179 A | 7/1970 | Reed |
| 3,604,247 A | 9/1971 | Gramain et al. |
| 3,666,999 A | 5/1972 | Moreland, Jr. et al. |

(List continued on next page.)

FOREIGN PATENT DOCUMENTS

| | | |
|---|---|---|
| DE | 31 38 514 A1 | 4/1983 |
| EP | 0 654 286 A1 | 12/1994 |
| FR | 2 510 257 | 1/1983 |
| WO | WO 92/15878 | 9/1992 |
| WO | WO 94/20832 | 9/1994 |
| WO | WO 99/10724 | 3/1999 |

OTHER PUBLICATIONS

Kensey, et al., Effects of Whole Blood Viscosity on Atherogenesis—J. of Invasive Cardiology V.9, 17, 1997.

(List continued on next page.)

Primary Examiner—Hezron Williams
Assistant Examiner—Jay L Politzer
(74) Attorney, Agent, or Firm—Caesar, Rivise, Bernstein, Cohen & Pokotilow, Ltd.

(57) ABSTRACT

An apparatus and method for determining the viscosity of the circulating blood of a living being over plural shear rates caused by a decreasing pressure differential by monitoring the changing weight of the blood, or the changing level of a column of blood over time. The apparatus and method utilize a riser, a capillary tube, a collector and a mass detector, such as a precision balance or a load cell, for monitoring the changing weight of a sample of fluid that flows through these components under the influence of the decreasing pressure differential; alternatively, the apparatus and method use a column level detector to monitor the changing level of the column of blood over time.

23 Claims, 16 Drawing Sheets

U.S. PATENT DOCUMENTS

| | | | |
|---|---|---|---|
| 3,680,362 | A | 8/1972 | Geerdes et al. |
| 3,699,804 | A | 10/1972 | Gassmann et al. |
| 3,713,328 | A | 1/1973 | Aritomi |
| 3,720,097 | A | 3/1973 | Kron |
| 3,782,173 | A | 1/1974 | Van Vessem et al. |
| 3,839,901 | A | 10/1974 | Finkle et al. |
| 3,853,121 | A | 12/1974 | Mizrachy et al. |
| 3,864,962 | A | 2/1975 | Stark et al. |
| 3,908,441 | A | 9/1975 | Virloget |
| 3,911,728 | A | 10/1975 | Fixot |
| 3,952,577 | A | 4/1976 | Hayes et al. |
| 3,967,934 | A | 7/1976 | Seitz et al. |
| 3,990,295 | A | 11/1976 | Renovanz et al. |
| 3,999,538 | A | 12/1976 | Philpot, Jr. |
| 4,083,363 | A | 4/1978 | Philpot, Jr. |
| 4,149,405 | A | 4/1979 | Ringrose |
| 4,165,632 | A | 8/1979 | Weber et al. |
| 4,193,293 | A | 3/1980 | Cavallari |
| 4,207,870 | A | 6/1980 | Eldridge |
| 4,302,965 | A | 12/1981 | Johnson et al. |
| 4,341,111 | A | 7/1982 | Husar |
| 4,417,584 | A | 11/1983 | Cathignol et al. |
| 4,426,878 | A | 1/1984 | Price et al. |
| 4,432,761 | A | 2/1984 | Dawe |
| 4,461,830 | A | 7/1984 | Philpot, Jr. |
| 4,517,830 | A | 5/1985 | Gunn et al. |
| 4,519,239 | A | 5/1985 | Kiesewetter et al. |
| 4,554,821 | A | 11/1985 | Kiesewetter et al. |
| 4,616,503 | A | 10/1986 | Plungis et al. |
| 4,637,250 | A | 1/1987 | Irvine, Jr. et al. |
| 4,643,021 | A | 2/1987 | Mattout |
| 4,680,957 | A | 7/1987 | Dodd |
| 4,680,958 | A | 7/1987 | Ruelle et al. |
| 4,750,351 | A | 6/1988 | Ball |
| 4,856,322 | A | 8/1989 | Langrick et al. |
| 4,858,127 | A | 8/1989 | Kron et al. |
| 4,899,575 | A | 2/1990 | Chu et al. |
| 4,947,678 | A | 8/1990 | Hori et al. |
| 5,099,698 | A | 3/1992 | Kath et al. |
| 5,181,415 | A | 1/1993 | Park et al. |
| 5,222,497 | A | 6/1993 | Ono |
| 5,224,375 | A | 7/1993 | You et al. |
| 5,257,529 | A | 11/1993 | Taniguchi et al. |
| 5,271,398 | A | 12/1993 | Schlain et al. |
| 5,272,912 | A | 12/1993 | Katsuzaki et al. |
| 5,327,778 | A | 7/1994 | Park |
| 5,333,497 | A | 8/1994 | Dag A et al. |
| 5,365,776 | A | 11/1994 | Lahmann et al. |
| 5,421,328 | A | 6/1995 | Bedingham |
| 5,447,440 | A | 9/1995 | Davis et al. |
| 5,491,408 | A | 2/1996 | Rousseau |
| 5,494,639 | A | 2/1996 | Grzegorzewski |
| 5,629,209 | A | 5/1997 | Braun, Sr. et al. |
| 5,686,659 | A | 11/1997 | Neel et al. |
| 5,792,660 | A | 8/1998 | Spillert et al. |
| 6,046,051 | A | 4/2000 | Jina ............................ 436/69 |
| 6,261,244 | B1 | 7/2001 | Kensey et al. .............. 600/573 |
| H93 | H | 7/1986 | Matta et al. |

OTHER PUBLICATIONS

Leonhardt, et al., Studies of Plasma Viscosity in Primary Hyperlipoproteinaemia—Atherosclerosis, V. 28, 29–40, 1977.

Ernst, et al., Cardiovascular Risk Factors and Hemorrheology: Physical fitness, Stress & Obesity—Atherosclerosis V. 59, 263–269, 1986.

Levenson, et al., Cigarette Smoking & Hypertension—Atherosclerosis V. 7, 572–577, 1987.

Rillaerts, et al., Blood Viscosity in Human Obesity; relation to glucose Tolerance & Insulin Status—Int'l Jrnl of Obesity, V. 13, 739–741, 1989.

Rosenson, R., Viscosity & Ischemic Heart Disease—Jrnl of Vascular Medicine & Biology, V.4, 206–212, 1993.

Letcher, et al., Direct Relationship between Blood Pressure & Blood Vioscosity in Normal and Hypertensive Subjects—Amer. Jrnl of Medicine, V. 70.

Zwick, K.J., The Fluid Mechanics of Bonding With Yield Stress Exposies, Dissortation—Univ. of Penna., PA, USA, 1–142, 1996.

Yarnell, et al., Fibrinogen, Viscosity & White Blood Cell Count Are Major Risk Factors for Ischemic Heart Disease—Circulation, V. 83, No. 3, Mar. 1991.

Tangney, et al., Postprandial changes in Plasma and Serum Viscosity and Plasma Lipids and Lipoproteins After an Acute Test Meal—Amer. Jrnl. Of Clinical Nutrition, V.65, p.36–40, 1997.

Seplowitz, et al., Effects of Lipoproteins on Plasma Viscosity—Athersclerosis, V. 38, p.89–95, 1981.

Rosenson, et al., Hyperviscosity Syndrome in Hypercholesterolemic Patient with Primary Billary Cirrhosis—Gastroenterology, V. 98, No. 5, 1990.

Lowe, et al., Blood Viscosity & Risk of Cardiovascular Events: Edinburgh Artery Study British Jrnl of Haematology, V. 96, 168–173, 1997.

Koenig, W., Blood Rheology Assoc. With cardiovascular Risk Factors & Chronic Cardiovascular Dis; Results of Epidemiologic Cross–sectional Study—Am. Col. Angiology, Paradise Is., Bahamas—Oct. 1987.

Hell, K., Importance of Blood Visco–elasticity in Arteriosclerosis Internl Col of Angiology, Montreaux, Switzerland, Jul. 1987.

Delaunois, A., Thermal method of Continuous Blood Velocity Measurements in Large Blood Vessels & Cardiac. Output Determination—Med. & Biol. Engineering, Mar. 1973, vol. 11, 201–205.

Nerem, et al., Fluid Mechanics in Atherosclerosis—Handbook of Bioengineering, Chap. 21, 20.24 to 21.22.

Litt, et al., Theory & Design of Disposable Clinical Blood Viscometer Biorrheology, vol. 25,697–712, 1988.

Cooke, et al., Automated Measurement of Plasma Viscosity by Capillary Viscometer—J. Clinical Pathology, vol. 31, 1213–1216, 1988.

Jiminez, et al., A Novel Computerized Viscometer/Rheometer—Rev. Sci Instru. vol. 65 (1), pp. 229–241, Jan. 1994.

Harkness, A New Instrument for Measurement of Plasma Viscosity—The Lancet, New Inventions, pp. 280–281, Aug. 10, 1963.

Pringle, et al., Blood Viscosity & Raynaurd's Disease—The Lancet, May 1965.

Walker, et al., Measurement of Blood Viscosity using a Conicylindrical Viscometer, Med. & Biol. Engineering, pp. 551557, Sep. 1976.

Kameneva, et al., Gender Difference in Rheologic Properties of Blood and Risk of Cardiovascular Diseases.

Kameneva, et al., Red Blood Cell Aging and Risk of Cardiovascular Diseases.

Ogura, et al., Measurement of Human Red Blood Cell Deformability Using a Single Micropore on a Thin Si3N4 Film, IEEE Trans. On Biomed. Engineering, vol. 38, No. 8, Aug. 1991.

Hausler, et al., A Newly Designed Oscillating Viscometer for Blood Viscosity Measurements, Biorrheology vol. 35, Nos. 4–5, pp. 397–404, 1996.

Martin, et al., Apparent Viscosity of Whole Human Blood at Various Hydrostatic Pressure–I. Studies on Anticoagulated Blood Employing a New Capillary Viscometer—Biorheology, 1976, vol. 11, pp. 439–446.

Reinhart et al., Rheologic Measurements on Small Samples with a New Capillary Viscometer—J. Clin. Lab, Dec. 1977, pp. 921–931.

Chmiel, H., A New Capillary Viscometer for Clinical Use, pp. 15–21.

Pall BPF 4 High Efficiency Leukocyte Removal Blood Processing Filter System 1983 Pall Corporation.

Qamar, MD., et al., The Goldman Algorithm Revisited: Prospective Evaluation of Competer–Derived Algorithm Versus Unaided Physician Judgement in Suspected Acute Myocardial Infarction pp. 1–7, Jan. 2000.

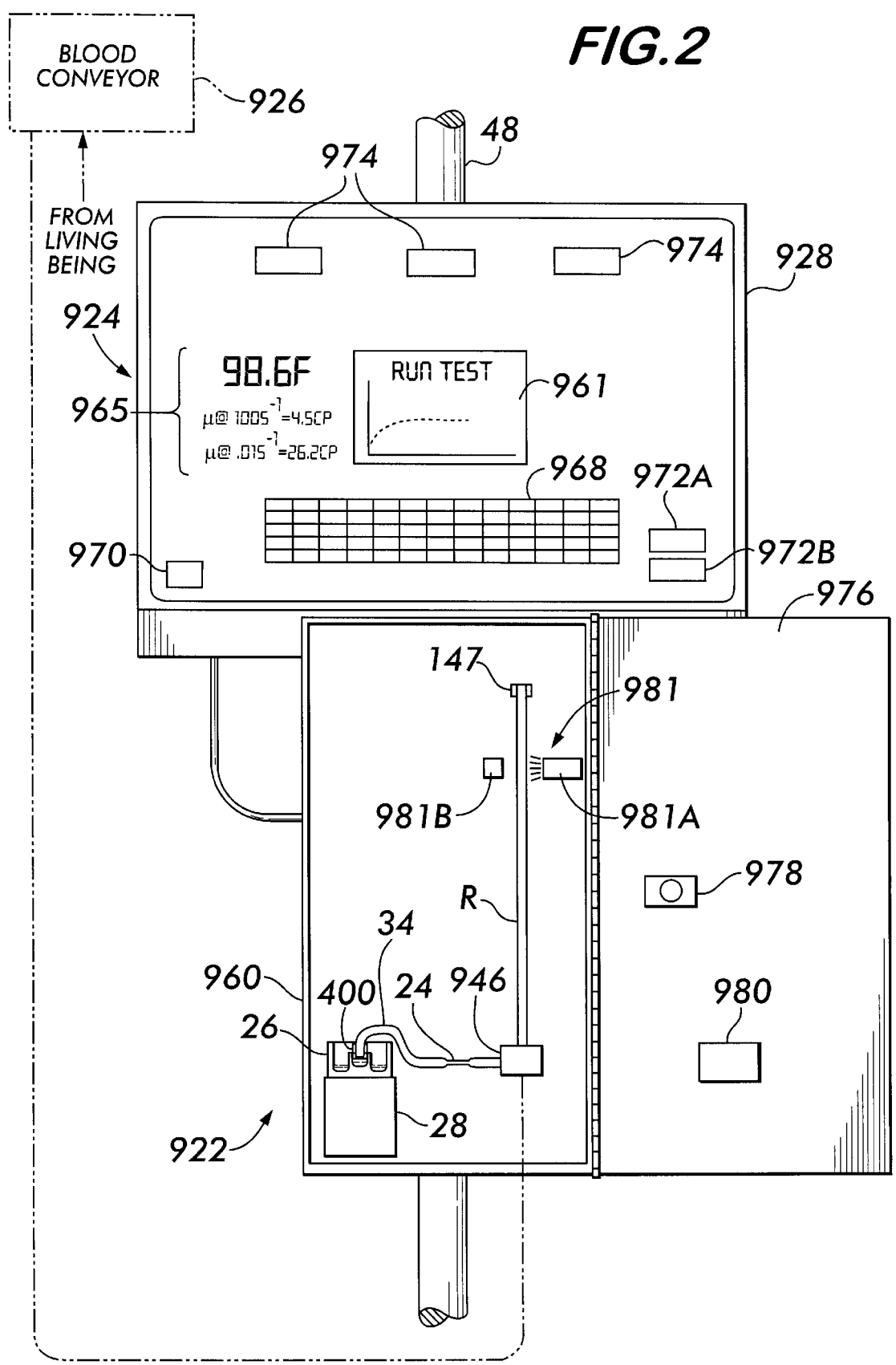

SINGLE RISER/SINGLE CAPILLARY BLOOD VISCOMETER USING MASS DETECTION OR COLUMN HEIGHT DETECTION

RELATED APPLICATIONS

This application is a Continuation-In-Part of application Ser. No. 09/789,350, filed Feb. 21, 2001, entitled Mass Detection Capillary Viscometer, which in turn is based on Provisional Application Serial No. 60/228,612 filed Aug. 29, 2000 entitled MASS DETECTION CAPILLARY VISCOMETER. This application is also a Continuation-in-Part of application Ser. No. 09/573,267 filed May 18, 2000, entitled DUAL RISER/SINGLE CAPILLARY VISCOMETER. The entire disclosures of all the above applications are incorporated by reference herein.

BACKGROUND OF THE INVENTION

A capillary viscometer is commonly used because of its inherent features such as simplicity, accuracy, similarity to process flows like extrusion dies, no free surface, etc. Viscous flow in capillary viscometry is firmly established both theoretically and experimentally. C. W. Macosko, *Rheology: Principles, Measurements, and Applications* (VCH, 1993). In fact, the capillary viscometer was the first viscometer and this device remains the most common for measuring viscosity for polymer solutions and other non-Newtonian fluids. However, most existing capillary viscometers produce viscosity measurement a shear rate at a time. In the case of Newtonian fluids the observation of the rate of flow at a single pressure drop is sufficient to define the flow behavior. However, in the case of non-Newtonian fluids, viscosity measurements need to be performed over a range of shear rates. In order to measure viscosity over a range of shear rates, it is necessary to repeat the measurement by varying either the driving pressure head or the capillary tube diameter, which leads to a time-consuming measurement requiring intensive labor. Hence, these methods are not suited for measuring the rheology of polymer fluids that may exhibit shear-dependent viscosities. Furthermore, application of such techniques often requires relatively large volumes of the test fluids. Therefore, there has been a need to develop a simple and labor-free viscometer which can measure the viscosity of fluids over shear rates at a time.

In U.S. Pat. No. 6,019,735 (Kensey et al.) and U.S. Pat. No. 6,077,234 (Kensey et al.), which are assigned to the same Assignee, namely Visco Technologies, Inc., of the present invention, there is disclosed a scanning-capillary-tube viscometer for measuring the viscosity of a fluid, e.g., circulating blood of a living being. Among other things, this scanning capillary tube viscometer discloses an apparatus that monitors the changing height of a column of fluid versus time in a riser that is in fluid communication with a living being's circulating blood. A further improvement of this type of scanning capillary tube viscometer is disclosed in application Ser. No. 09/439,735 entitled DUAL RISER/SINGLE CAPILLARY VISCOMETER, which is assigned to the same Assignee as the present invention, namely, Visco Technologies, Inc. and whose entire disclosure is incorporated by reference herein. In that application, a U-shaped tube structure is utilized that generates a falling and rising column of test fluid that is driven by a decreasing pressure differential for moving these columns of fluid through a plurality of shear rates, which is necessary for non-Newtonian fluid (e.g., blood) viscosity determinations. Such an apparatus can produce viscosity data in a low shear range (e.g., approximately 0.02 $s^{-1}$).

However, there is a need for an alternative mechanism of monitoring the changing column of fluid over time, such as detecting the changing mass of the column of fluid, as set forth in the present application. The key principle of the mass-detection-capillary viscometer is that both flow rate and pressure drop at a capillary tube can be determined by a single measurement of collected fluid mass variation with time using a load cell. Thus, there also remains a need to develop a viscosity determination in a quasi-steady capillary flow and to measure the viscosity of non-Newtonian fluids (e.g., polymer solutions, circulating blood of a living being, etc.) over a range of shear rates.

SUMMARY OF THE INVENTION

An apparatus for determining the viscosity of the circulating blood of a living being over plural shear rates using a decreasing pressure differential. The apparatus comprises: a lumen (e.g., a riser tube) being positioned at an angle to a horizontal reference greater than zero degrees, wherein the lumen comprises a first end and a second end and wherein the first end is exposed to atmospheric pressure and wherein the lumen comprises a first known dimension (e.g., the diameter of the lumen); a flow restrictor (e.g., a capillary tube) having an inlet and an outlet wherein the outlet is arranged to deliver any blood that passes therethrough to a collector, and wherein the flow restrictor includes some known dimensions (e.g., the length and diameter of the flow restrictor); a valve coupled to the vascular system of the living being at a first port and wherein the valve comprises a second port coupled to the second end and a third port is coupled to the inlet; a sensor for detecting the movement of the blood over time (e.g., a mass detector, a column level detector, etc.) through the apparatus and wherein the sensor generates data relating to the movement of the blood over time; a processor, the valve to create a column of blood in the first lumen and the flow restrictor and to establish a pressure differential between the first end and the outlet, and wherein the column of blood moves through the lumen and the flow restrictor at a first shear rate caused by the pressure differential and wherein the movement of the column of blood causes the pressure differential to decrease from the first shear rate for generating the plural shear rates; and wherein the processor calculates the viscosity of the blood based on the data relating to the movement of the column of blood over time, the first known dimension of the lumen and the some known dimensions of the flow restrictor.

A method for determining the viscosity of the circulating blood of a living being over plural shear rates caused by a decreasing pressure differential. The method comprises the steps of: (a) providing a lumen having a first end and a second end and positioned at an angle to a horizontal reference greater than zero degrees, and wherein the lumen has a first known dimension (e.g., the diameter of the lumen) and wherein the first end is exposed to atmospheric pressure; (b) diverting a portion of the circulating blood into the lumen through the second end to form a column of blood therein; (c) coupling an inlet of a flow restrictor to the second end of the lumen to establish a pressure differential between the first end and the outlet and wherein the flow restrictor has an outlet that is arranged to deliver any blood that passes therethrough to a collector and wherein the flow restrictor has some known dimensions (e.g., the length and the diameter of the flow restrictor); (d) controlling the column of blood to form a continuous column of blood in the lumen and the flow restrictor, and wherein the column of blood moves through the lumen and the flow restrictor at a first shear rate caused by the pressure differential and wherein the movement of the column of blood causes the pressure differential to decrease from the first shear rate for generating the plural shear rates; (e) providing a sensor for detecting the movement of the column of blood over time (e.g., a mass detector, a column level detector, etc.) as the column of blood moves and passes from the outlet into the collector while maintaining the outlet submerged in blood that has collected in the collector, and wherein the sensor generates data regarding the movement; and (f) calculating the viscosity of the blood based on the generated data, the first known dimension and the some known dimensions.

An apparatus for determining the viscosity of the circulating blood of a living being over plural shear rates using a decreasing pressure differential. The apparatus comprises: a lumen (e.g., a riser tube) being positioned at an angle to a horizontal reference greater than zero degrees, and wherein the lumen comprises a first end and a second end and wherein the lumen also comprises a first known dimension (e.g., the diameter of the lumen); a flow restrictor (e.g., a capillary tube) having an inlet and an outlet wherein the outlet is arranged to deliver any blood that passes therethrough to a collector and wherein the inlet is coupled to the second end and wherein the flow restrictor includes some known dimensions (e.g., the length and diameter of the flow restrictor); a valve coupled to the vascular system of the living being at a first port and wherein the valve comprises a second port coupled to the first end; a sensor for detecting the movement of the blood over time (e.g., a mass detector, a column level detector, etc.) through the apparatus and wherein the sensor generates data relating to the movement of the blood over time; a processor, coupled to the valve and the sensor wherein the processor is arranged to operate the valve to create a column of blood in the first lumen and the flow restrictor and to establish a pressure differential between the first end and the outlet and wherein the column of blood moves through the lumen and the flow restrictor at a first shear rate caused by the pressure differential and wherein the movement of the column of blood causes the pressure differential to decrease from the first shear rate for generating the plural shear rates; and wherein the processor calculates the viscosity of the blood based on the data relating to the movement of the column of blood over time, the first known dimension of the lumen and the some known dimensions of the flow restrictor.

A method for determining the viscosity of the circulating blood of a living being over plural shear rates caused by a decreasing pressure differential. The method comprises the steps of: (a) providing a lumen (e.g., a riser tube) having a first end and a second end and positioned at an angle to a horizontal reference greater than zero degrees and wherein the lumen has a first known dimension (e.g., the diameter of the lumen); (b) coupling an inlet of a flow restrictor (e.g., a capillary tube) to said second end and arranging an outlet of the flow restrictor to deliver any blood that passes therethrough to a collector and wherein the flow restrictor has some known dimensions (e.g., the length and diameter of the flow restrictor); (c) diverting a portion of the circulating blood into the lumen through the first end to form a column of blood in the lumen and the flow restrictor and to establish a pressure differential between the first end and the outlet; (c) exposing the first end to atmospheric pressure to cause the column of blood to move through the lumen and the flow restrictor, wherein the movement of the column of blood causes the pressure differential to decrease from the first shear rate for generating the plural shear rates; (d) providing a sensor for detecting the movement of the column of blood over time (e.g., a mass detector, a column level detector, etc.) as the column of blood moves and passes from the outlet into the collector while maintaining the outlet submerged in blood that has collected in the collector and wherein the sensor generates data regarding the movement; and (e) calculating the viscosity of the blood based on the generated data, the first known dimension and the some known dimensions.

An apparatus for determining the viscosity of the circulating blood of a living being over plural shear rates using a decreasing pressure differential. The apparatus comprises: a first lumen (a riser tube) being positioned at an angle to a horizontal reference greater than zero degrees and wherein the lumen comprises a first end and a second end and wherein the first end is exposed to atmospheric pressure and wherein the lumen comprises a first known dimension (e.g., the diameter of the first lumen); a flow restrictor (e.g., a capillary tube) having an inlet and an outlet wherein the inlet is coupled to the second end and wherein the flow restrictor includes some known dimensions (e.g., the length and diameter of the flow restrictor); a valve coupled to the vascular system of the living being at a first port wherein the valve comprises a second port coupled to the outlet and a third port coupled to an input of a second lumen (e.g., an adaptor, etc.) arranged to deliver any blood that passes therethrough to a collector through an output of the second lumen; a sensor for detecting the movement of the blood over time (e.g., a mass detector, a column level detector, etc.) through the apparatus and wherein the sensor generates data relating to the movement of the blood over time; a processor, coupled to the valve and the sensor and wherein the processor is arranged to operate the valve to create a column of blood in the first lumen and the flow restrictor and to establish a pressure differential between the first end and the output wherein the column of blood moves through the lumen and the flow restrictor at a first shear rate caused by the pressure differential and wherein the movement of the column of blood causes the pressure differential to decrease from the first shear rate for generating the plural shear rates; and wherein the processor calculates the viscosity of the blood based on the data relating to the movement of the column of blood over time, the first known dimension of the first lumen and the some known dimensions of the flow restrictor.

DESCRIPTION OF THE DRAWINGS

The invention of this present application will be readily appreciated as the same becomes better understood by reference to the following detailed description when considered in connection with the accompanying drawings wherein:

FIG. 2 is a front view of an embodiment of the MDCBV;

DETAILED DESCRIPTION OF THE PREFERRED EMBODIMENTS

Figure 1:
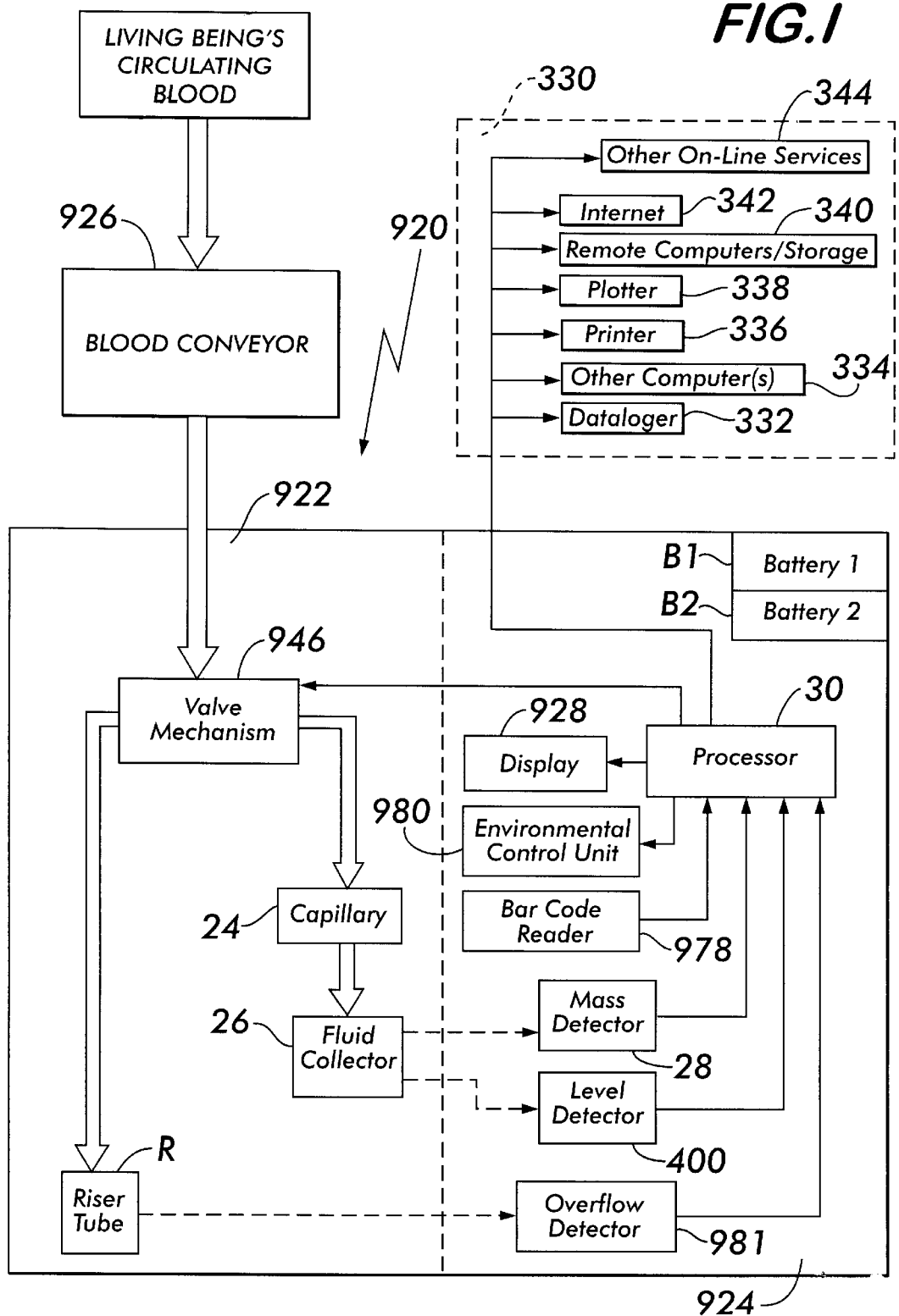
FIG. 1 is a block diagram of a single riser/single capillary (SRSC) blood viscometer using mass detection which is also referred to as a mass detection capillary blood viscometer (MDCBV)

The present invention, generally referred to as a single riser/single capillary (SRSC) blood viscometer, uses a single riser tube and a single flow restrictor (e.g., a capillary tube) structure for determining the viscosity of the circulating blood of a living being.

Although the SRSC blood viscometer can be implemented in a number of ways, two exemplary apparatus/methods are set forth below. The first implementation uses the SRSC structure along with mass detection and hence is hereinafter referred to as a mass detection capillary blood viscometer (MDCBV) 20. The second implementation uses the SRSC structure along with column height detection and hence is hereinafter referred to as a column height detection capillary (CHDC) blood viscometer 1020.

Referring now in detail to the various figures of the drawing wherein like reference characters refer to like parts, there is shown at 920 a mass detecting capillary blood viscometer (MDCBV).

The MDCBV 920 basically comprises a blood receiver 922 and an analyzer/output portion 924. The patient is coupled to the MDCBV 920 through a circulating blood conveyor 926, e.g., a needle, an IV needle, an in-dwelling catheter, etc., or any equivalent structure that can convey circulating blood from a patient to the MDCBV 920. As will be discussed in detail later, the analyzer/output portion 924 provides a display 28 for presenting the viscosity information, as well as other information to the operator. The analyzer/output portion 924 may also provide this information to other suitable output means 330, such as a datalogger 332, other computer(s) 334, a printer 336, a plotter 338, remote computers/storage 340, to the Internet 342 or to other on-line services 344.

Figure 4:
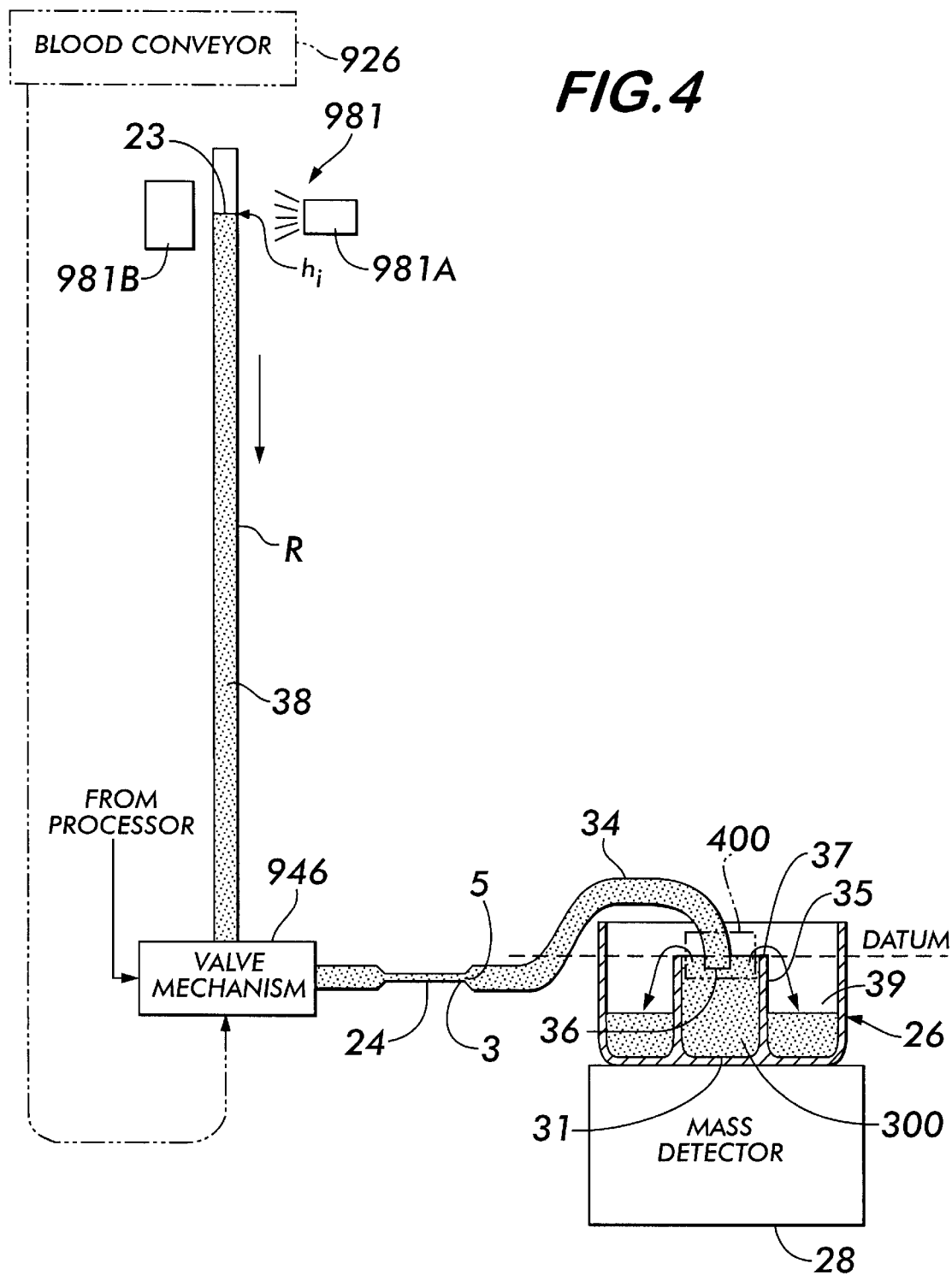
FIG. 4 is a functional diagram of the MDCBV.

The blood receiver 922 basically comprises a valve mechanism 946 coupled to a riser tube R on one side and coupled to a flow restrictor 24 (e.g., a capillary tube) on the other side. The output of the flow restrictor 24 is directed into a fluid collector 26 via an adaptor 34. When the blood conveyor 926 is coupled to the blood receiver 922, the valve mechanism 946 controls the flow of blood into the blood receiver 922, as will be discussed in detail later. The upper end of the riser tube R is exposed to atmospheric pressure. The riser tube R may be positioned at any non-zero angle to a horizontal reference position (e.g., the datum line as shown in FIG. 4); one exemplary position is at a vertical orientation with respect to the datum line as shown in FIG. 4.

It should be understood that the blood receiver 922 may be disposable or non-disposable. As will be discussed in detail later, where the blood receiver 922 is disposable, the components (valve mechanism 946, riser tube R and flow restrictor 24) are releasably secured in a blood receiver housing 962 that can be quickly and easily inserted, used during the viscosity test run and then quickly and easily removed for disposal; another disposable blood receiver 922 is then inserted in preparation for the next viscosity test run. On the other hand, where the blood receiver 922 is non-disposable, the components (valve mechanism 946, riser tube R and flow restrictor 24) can be thoroughly washed and cleaned in place in preparation for the next viscosity test run.

It should be understood that the flow restrictor 24 does not necessarily have to be an elongated tube but may comprise a variety of configurations such as a coiled capillary tube.

The analyzer/output portion 924 basically comprises a mass detector 28, a level detector 400, a processor 30, the display 928, a bar code reader 978, an environmental control unit 980, and overflow detector 981, a first battery B1 and a second back-up battery B2. The fluid collector 26 is positioned on top of the mass detector 28 which monitors the increasing mass of blood collecting in the fluid collector 26. The overflow detector 981 ensures that when the column of blood is generated, no blood overflows the riser R. The processor 30 (e.g., a "386" microprocessor or greater, or any equivalent) is arranged to analyze the data from the mass detector 28 and to calculate the blood viscosity therefrom, as will also be discussed in detail later. Furthermore, the processor 30 also controls the display 928 for providing the viscosity information and the other information to the operator as well as to the other output means 330. The processor 30 also controls the valve mechanism 946 based on the data from the mass detector 28, as will be discussed later. Battery B1 provides all of the requisite power to the analyzer/output portion 24, with battery B2 serving as a back-up power supply. The bar code reader 978, the environmental control unit 980 and the level detector 400 will be described later.

In general, via the use of the valve mechanism 946, a column of blood 38 is initially generated in the riser R and then that column of blood 38 is permitted to fall through the riser tube R, through the flow restrictor 24 and into the fluid collector 26. This movement of blood can be represented by a height vs. time relationship (FIG. 1A) with regard to the column of blood in the riser R and by a mass vs. time relationship (FIG. 1B) with regard to the blood being received in the fluid collector 26.

Figure 3:
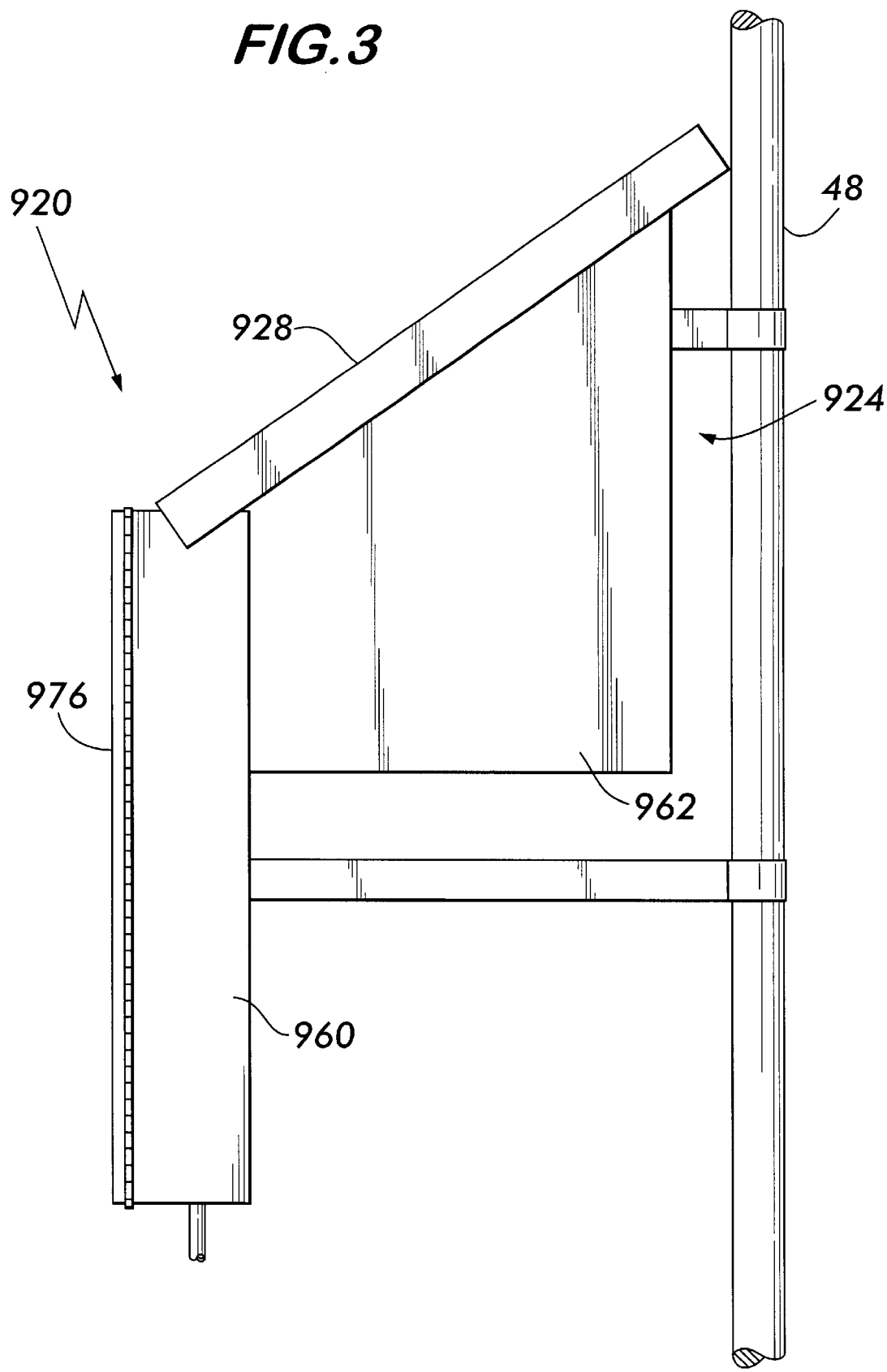
FIG. 3 is a side view of the MDCBV.

As shown more clearly in FIGS. 2–3, the preferred embodiment of the MDCBV 920 comprises the blood receiver 922 and the analyzer/output portion 924 contained in respective housings 960 and 962, each of which can be releasably secured to a common frame, e.g., a conventional intravenous (IV) pole 48. In this configuration, the analyzer/ output portion 924 can be positioned in an inclined orientation (see FIG. 3) to facilitate user operation and viewing of the display 928. However, it should be understood that the respective housing constructions are exemplary, and others can be incorporated without limiting the scope of this invention.

The display 928 may comprise any suitable conventional devices, e.g., an ELD (electroluminescent display) or LCD (liquid crystal display) that permits the visualization of both text and graphics. The resolution of this display 928 is preferably 800×600 VGA or above. Furthermore, while the preferred embodiment utilizes a touch screen display which incorporates, among other things:

graphical display 961 instruction, and/or data, display 965 (which also includes the command line display shown as "RUN TEST"; e.g., "TESTING", "TEST IN PROGRESS," etc.)

alphanumeric keypad 968 emergency stop button 970 battery status indicators, 972A and 972B function buttons 974, it should be understood that any equivalent display device is within the broadest scope of the invention. Thus, any number of user interfaces and buttons may be available through the display 928. Therefore the invention 920 is not limited to the embodiment that is shown in FIG. 2. Moreover, the display 928 can be operated to minimize or maximize, or overlay any particular graphic or text screen, as is available in any conventional object-oriented operating system, such as Microsoft® WINDOWS.

The lower housing 960 comprises the blood receiver 922 and the mass detector 28. In the preferred embodiment, the mass detector 28 may comprise a precision balance, or load cell, such as The Adventurer™ by Ohaus Corporation of Florham Park, N.J. Thus, as the collector 26 collects more of the blood during the viscosity test run, the changing mass value is transmitted to the processor 30 from the mass detector 28 for viscosity determination; in particular, the mass detector 28 generates an electrical signal that corresponds to the mass variation in time. It should be understood that the term "mass" may be interchanged with the term "weight" for purposes of this invention. It should also be understood that the connection between the mass detector 28 and the processor 30 is bi-directional; this allows the processor 30 to reset the mass detector 28 in preparation for a new test run.

It should also be understood that although it is preferable to have the riser tube R in a vertical position, it is within the broadest scope of this invention to have the riser tube R oriented at any angle greater than zero degrees, with respect to a horizontal reference (e.g., datum line shown in FIG. 4).

Where the blood receiver 922 is disposable, it is releasably secured in the housing 960 such that once a test run is completed and/or a new patient is to be tested, all of the lumens (e.g., the riser tube R, the capillary 24, the adaptor 34 and the valve mechanism 946) can be easily/quickly removed, disposed of and a new set inserted. For example, a bracket 147 (FIG. 2) may be used to releasably secure the upper portion of the riser tube R.

A door 976 (which can be vertically or horizontally hinged to the housing 960) is provided to establish a temperature-controlled environment during the test run. In particular, the door 976 also supports an environmental control unit 980 (e.g., a heater, fan and/or thermostat) such that when it is closed in preparation for the test, the flow restrictor 24 is then heated (or cooled) and maintained throughout the test run at the same temperature and environment as the living being. Prior to the run, the living being's temperature is taken and the operator enters this temperature (via the touch screen display 928). The environmental control unit 980 then operates to achieve and maintain this temperature. It should be noted that it is within the broadest scope of this invention to include a environmental control unit 980 that achieves and maintains the entire blood receiver 922 at the patient's temperature during the run. By properly maintaining the temperature throughout the test run, the effects of any temperature variation in the viscosity measurement is minimized.

The door 976 may also support the bar code reader 978. The bar code reader 978 automatically reads a bar code (not shown) that is provided on the riser tube R. The bar code contains all of the predetermined data regarding the characteristics of the flow restrictor 24 (e.g., its length and diameter) and the characteristics of the riser tube R. This information is passed to the processor 30 which is then used to determine the viscosity.

The batteries B1/B2 may each comprise a 12 VDC, 4 amp-hour battery, or any equivalent power supply (e.g., batteries used in conventional lap-top computers such as lithium ion batteries). The display 928 provides the status indicators 972A/972B for each battery in the MDCBV 920. In particular, when the MDCBV 920 is operating off of battery B1, the two battery indicators 972A/972B appear on the display 928. However, once battery B1 is depleted, the battery B1 indicator 972A disappears and the battery B2 indicator 972B blinks to warn the operator that the MDCBV 920 is now operating off of the back-up battery B2 and re-charge of battery B1 is necessary.

The preferred fluid collector 26 of the present invention is similar to that disclosed in application Ser. No. 09/789,350. In particular, the collector 26 comprises an inner circular wall 35 that divides the collector 26 into a central portion 31 and an annular portion 39. The central portion 31 collects the blood as it enters the collector 26. The column of blood 38 falls through the riser tube R, the flow restrictor 24, the adaptor 34 and then into the central portion 31. Any overflow spills into the annular portion 39.

It should be understood that the phrase "column of blood 38" is meant to cover the continuous element of blood that occupies the riser tube R as well as the blood that occupies the flow restrictor 24 and the adaptor 34.

To minimize any surface tension effects that would normally occur if an open end 36 of the adaptor was positioned above the level of collected blood 300 in the central portion 31, it is necessary to begin collecting mass vs. time data only when the open end 36 of the adaptor 34 is submerged within the collected blood 300. This is shown most clearly in FIG. 4. In order to accomplish this, the open end 36 of the adaptor 34 is placed appropriately below the datum line (e.g., the top edge 37 of the inner wall 35 of the preferred collector 26) and the level detector 400 is provided for detecting when the collected blood 300 has reached the datum level. The level detector 400 informs the processor 30 when this event has occurred. Thus, the processor 30 is able to determine those mass vs. time data points where surface tension effects are minimized. The level detector 400 can be implemented in various ways known to those skilled in art, e.g., float sensors, tuning fork sensors, ultrasonic sensors, optical sensors, proximity sensors, capacitance sensors, etc. and all of which generate an electrical signal when a particular fluid level has been reached. An exemplary sensor is the ColeParmer EW-20603-22 Capacitive Level Sensor.

It should be understood that the output side 3 of the flow restrictor 24 can be integrally formed with the input side 5 of the adaptor 34.

The concept of the blood viscosity determination using the MDCBV 920 is that a portion of the circulating blood of the living being is diverted from the living being using the blood conveyor 926 into the blood receiver 922 to create a column of blood 38 (FIG. 4) in the riser tube R. Next, the column of blood 38 is allowed to fall and collect in the fluid collector 26 over time, whereby the changing mass of this collector 26 is monitored over time. From this mass vs. time data and based on the characteristics of the flow restrictor 24 and the riser tube R, the circulating blood viscosity can be determined. In addition, where the blood exhibits yield stress, $\tau_y$, a residual amount of the column of blood 38 remains in the riser tube R after a long period of time at the end of the viscosity test run; furthermore, there are surface tension effects that also contribute to this residual amount of the column of blood 38 as a result of the gas-liquid interface 23 (FIG. 4). The height of this residual column of fluid is known as $\Delta h_\infty$, where $\Delta h = h(t) -$ datum level and where $h(t)$ represents the height of the column of blood 38 in the riser tube R at any time; the term $h_\infty$ (FIG. 1A) represents the final height of the column of blood 38 in the riser tube R at the end of the test run after a long period of time. As will also be discussed later, the viscosity determination of the blood can be determined using the MDCBV 920 without the need to determine $h(t)$ or the initial position, $h_i$, of the column of blood 38 in the riser tube R at which data is collected.

Figure 5A:
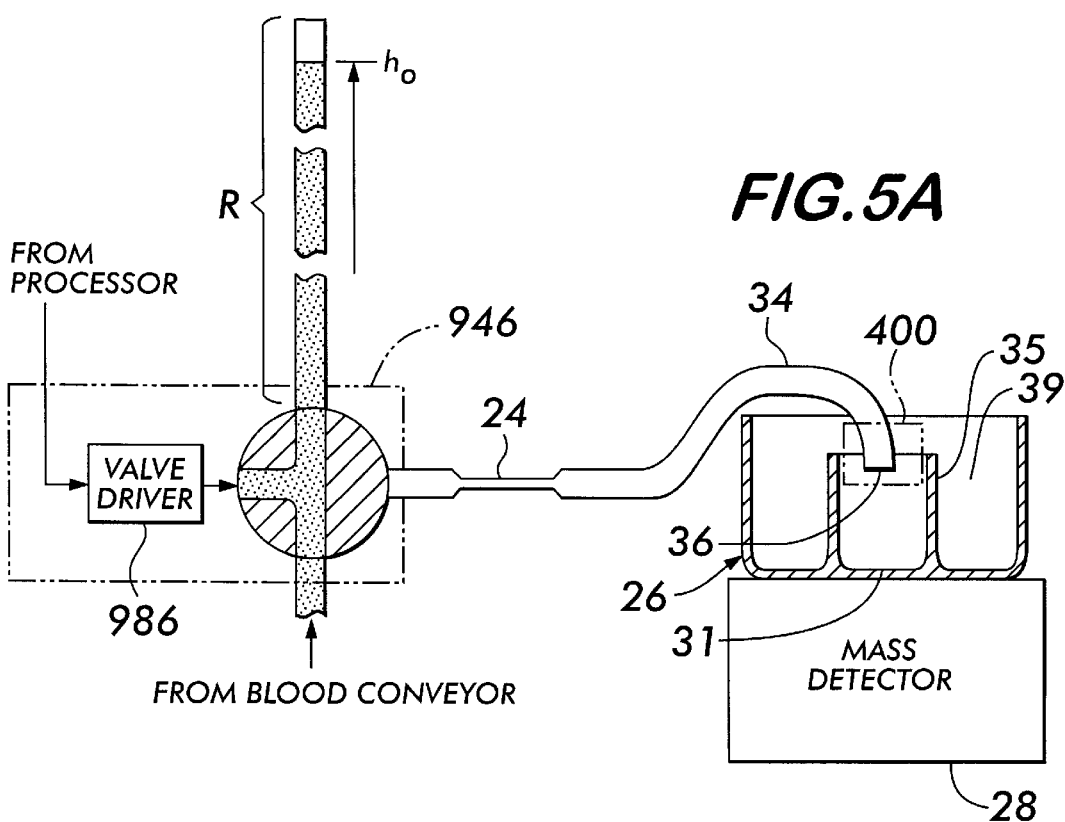
FIG. 5A is a functional diagram of the valve activated to create a column of blood.

To obtain accurate data, it is important to "wet" all of the lumens, namely, the riser tube R, the valve mechanism 946, the flow restrictor 24 and the adaptor 34 before data is taken. As a result, in order to generate the column of blood 38 and then allow it to fall, the valve mechanism 946 must be operated as follows: When the viscosity test run is initiated, the processor 30 activates the valve mechanism 946 by commanding a valve driver 986 (e.g., a 500 mA solenoid, or stepper motor, etc.) which rotates the valve into the position shown in FIG. 5A. This allows the diverted portion of the circulating blood to flow up into the riser tube R to create the column of blood 38. When the overflow detector 981 detects a predetermined height, $h_0$, of the column of blood 38, the overflow detector 981 informs the processor 30 which then commands the valve driver 986 to rotate the valve into the position shown in FIG. 5B. As a result, the column of blood 38 begins to fall through the riser tube R, through the valve mechanism 946, into the flow restrictor 24, through the adaptor 34 and into the central portion 31 of the fluid collector 26. As mentioned earlier, the processor 30 is informed by the level detector 400 when the open end 36 of the adaptor 34 is submerged under the level of the collected blood 300 in order to minimize any surface tension effects. Next, the valve driver 986 is commanded by the processor 30 into the position shown in FIG. 5C which halts all motion of the column of blood 38. The initial position of the column of blood, hi, is thereby established for viscosity determination purposes, as will be discussed later. Finally, the processor 30 commands the valve driver 986 to rotate the valve into the position shown in FIG. 5D and the column of blood 38 begins falling while data is collected.

The overflow detector 981 may comprise an optical source 981A, e.g., a light emitting diode (LED) and a photodetector 981B for detecting emitted light from the optical source 981A; once the upper end of the column of blood 38 interrupts the emitted light, the photodetector 981B informs the processor 30 which operates the valve mechanism 946, as discussed previously. It should be understood that this implementation of the overflow detector 981 is exemplary only and that it is within the broadest scope of this invention to include all methods of level detection known to those skilled in the art of detecting the level of the column of blood 38 in the riser tube R.

Figure 6:
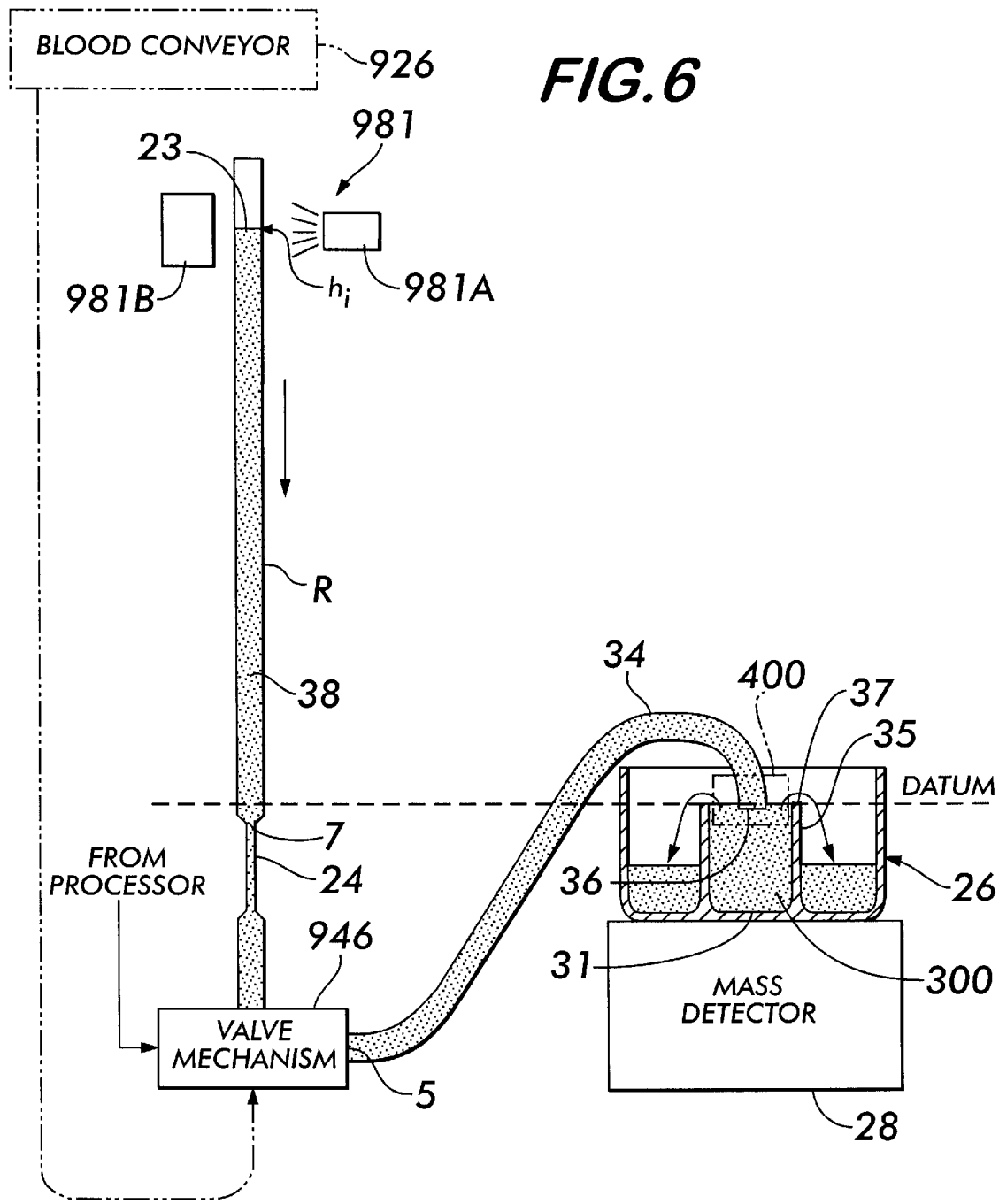
FIG. 6 is a functional diagram of a second embodiment of the MDCBV having an alternative position of the capillary tube.

FIG. 6 depicts a second embodiment of the MDCBV 920 wherein the flow restrictor 24 forms the lower end of the riser tube R, rather than being located on the other side of the valve mechanism 946. As a result, the input side 5 of the adaptor 34 is coupled to the valve mechanism 946. For proper operation, the datum line needs to be above the input side 7 of the flow restrictor 24, as shown in FIG. 6. Other than that, the operation of this variation is governed by the same equations for the first embodiment as will be discussed below.

Figure 7:
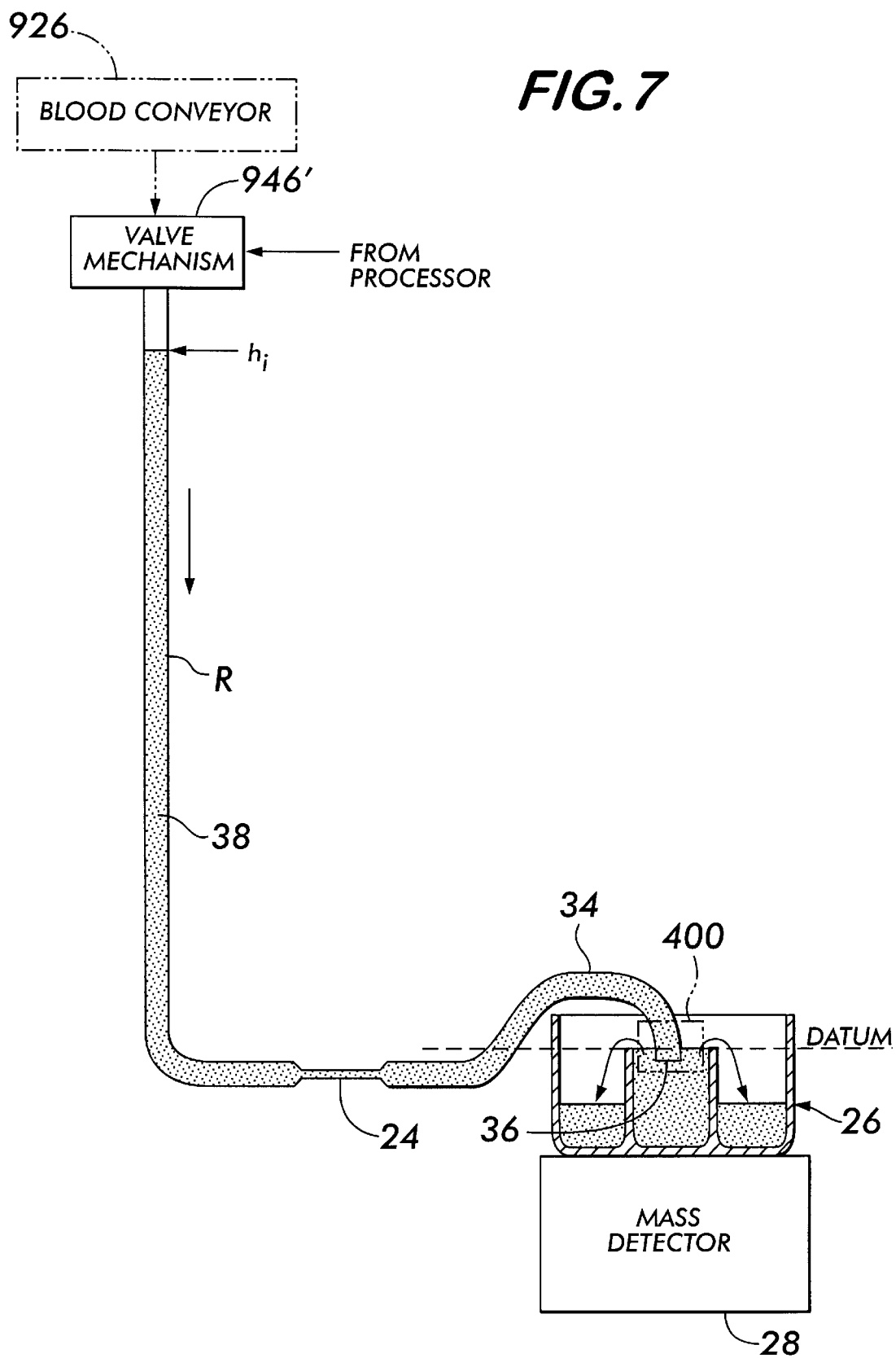
FIG. 7 is a functional diagram of a third embodiment of the MDCBV having an alternative position of the valve mechanism.
Figure 8A:
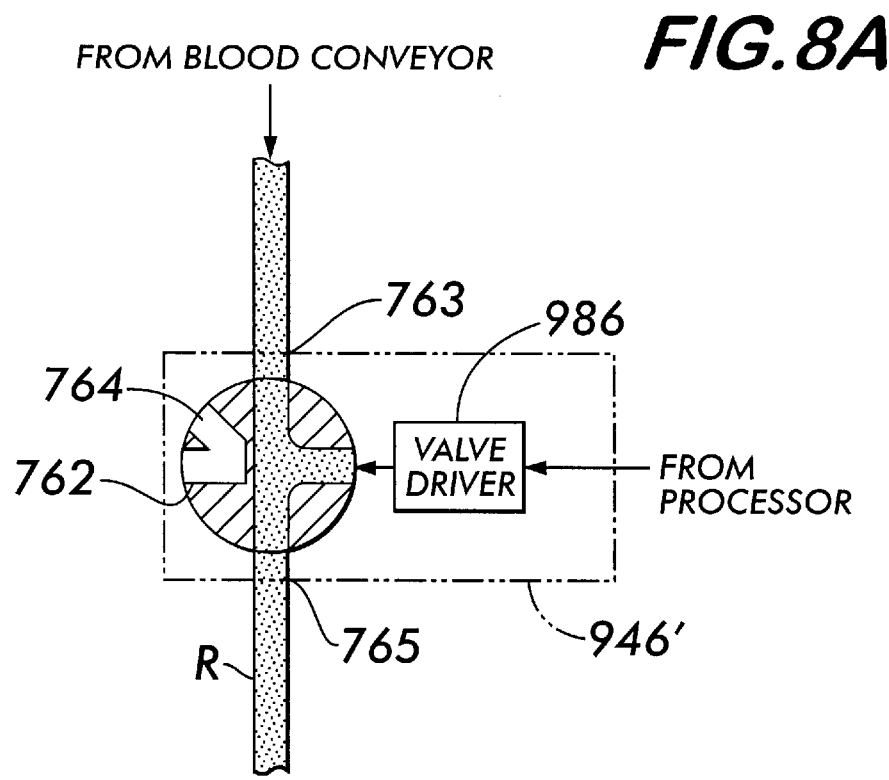
FIG. 8A is a functional diagram of the valve mechanism of FIG. 7 activated to create a column of blood.
Figure 8B:
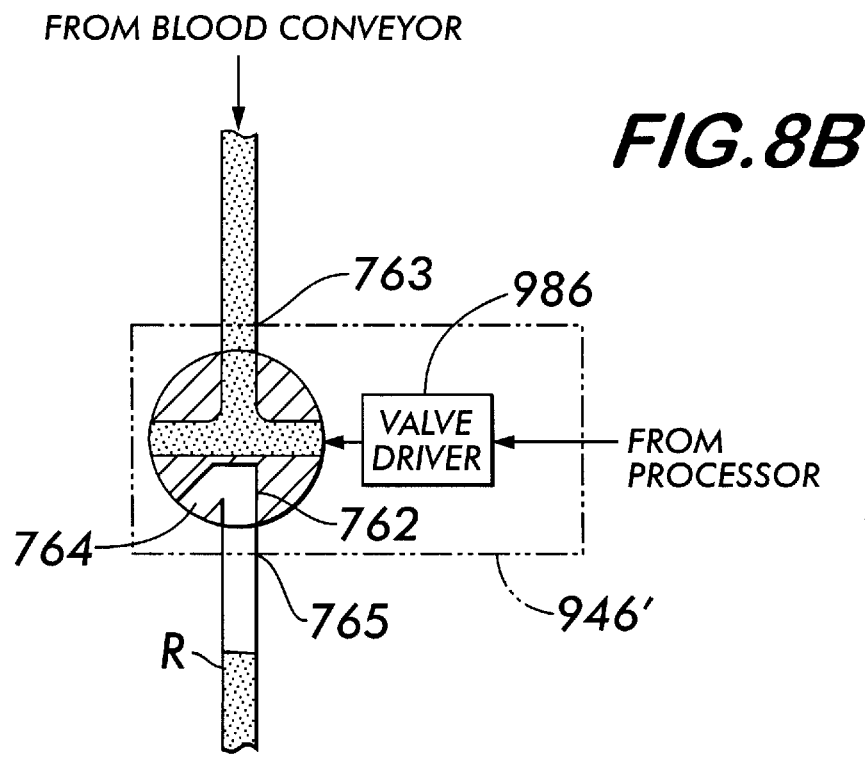
FIG. 8B is a functional diagram of the valve mechanism of FIG. 7 activated to permit the column of blood to move and be collected in a collector.

FIG. 7 depicts a third embodiment of the MDCBV 920 wherein the valve mechanism 946' is positioned at the top of the riser tube R, rather than at the bottom. The advantage of this valve mechanism 946' position is that there is no need to first fill the riser tube R to a predetermined level before proceeding with the test run; instead, in accordance with the valve mechanism 946' operation as shown in FIGS. 8A–8B, the test run proceeds with the processor 30 commanding the valve driver 986 to rotate the valve to the position shown in FIG. 8A and then the processor 30 stops any more input flow from the blood conveyor 926 as shown in FIG. 8B. In particular, as used in this embodiment, the blood conveyor 926 is coupled to the valve mechanism 946' at a port 763; the top end of the riser tube R is coupled to the valve mechanism 946' at a port 765. The valve mechanism 946' also includes a vent coupler 762 that couples the top of the riser R to a third port 764 that is exposed to atmospheric pressure; thus when the valve is rotated into the position shown in FIG. 8B, the blood in the riser tube R will flow downwards. Again, it should be emphasized that to minimize any surface tension effects, the level detector 400 informs the processor 30 when the open end of the adaptor 34 is submerged in the collected blood 300. Other than that, the operation of this variation is governed by the same equations mentioned previously.

MDCBV Theory of Operation

The concept of the blood viscosity determination using the MDCBV 920 is based on the discussion of determining the viscosity of non-Newtonian fluids, such as blood, as discussed in detail in application Ser. No. 09/789,350, whose entire disclosure is incorporated by reference herein. The MDCBV 920 basically comprises a cylinder (i.e., the riser tube R) having a diameter, $\phi_R$, into which a portion of the circulating blood of the living being is diverted for viscosity analysis. The bottom of the riser tube R is coupled to the flow restrictor 24 (e.g., a capillary tube), having a diameter $\phi_c$ and a length $L_c$. It is preferable that the diameter of the adaptor 34 be similar to the diameter of the riser tube R, $\phi_R$.

Figure 1A:
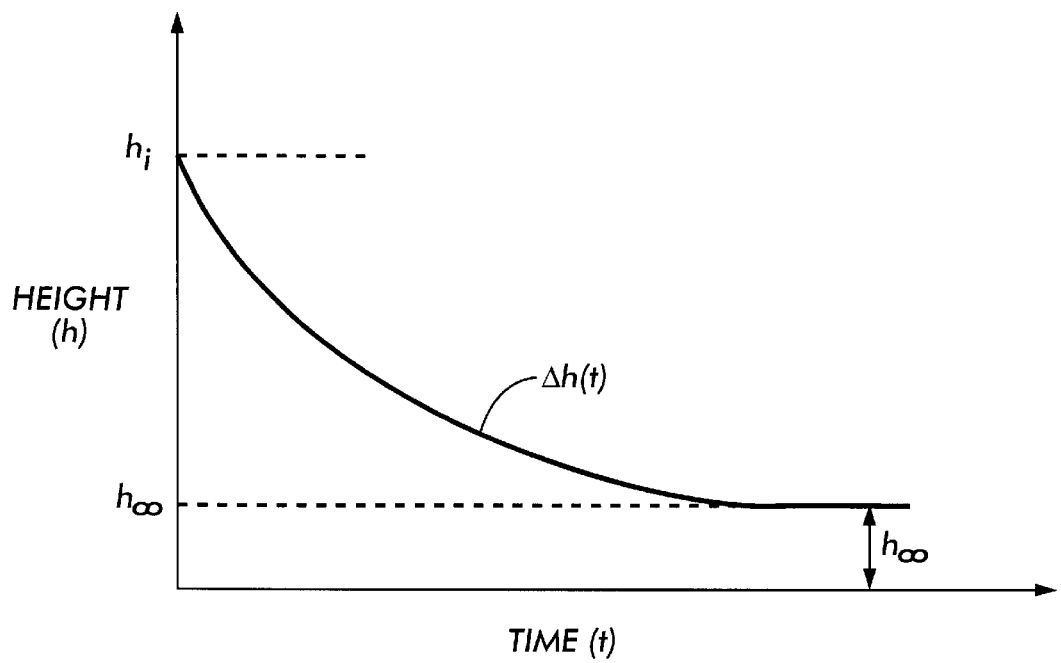
FIG. 1A is a height vs. time plot of the blood column in the riser tube of the MDCBV.
Figure 1B:
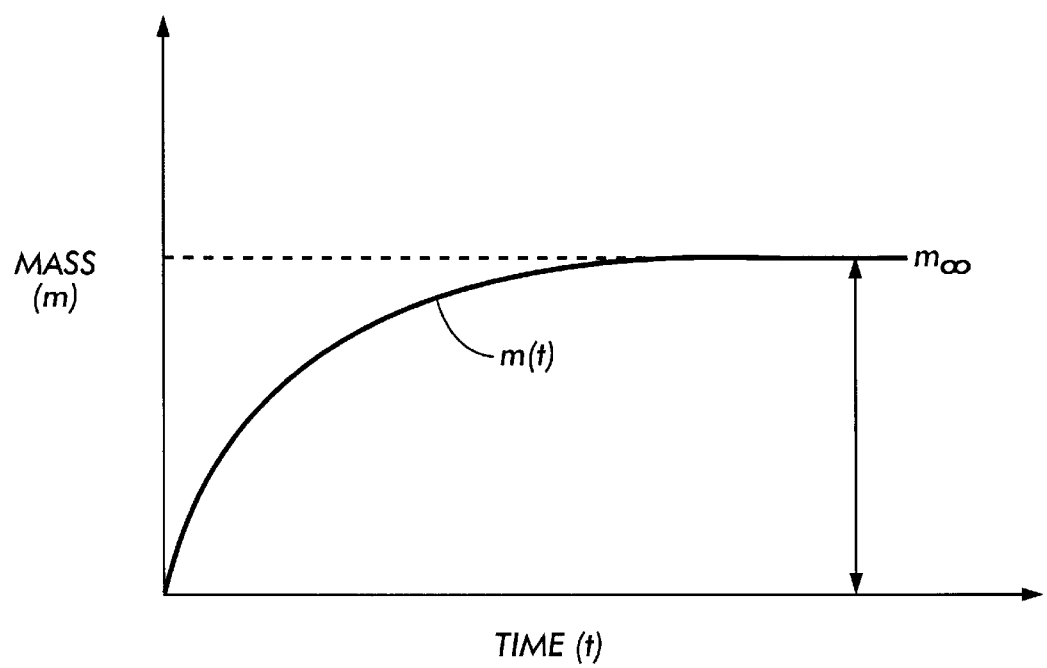
FIG. 1B is a mass vs. time plot of the blood as it is collected in the collector of the MDCBV.
Figure 5B:
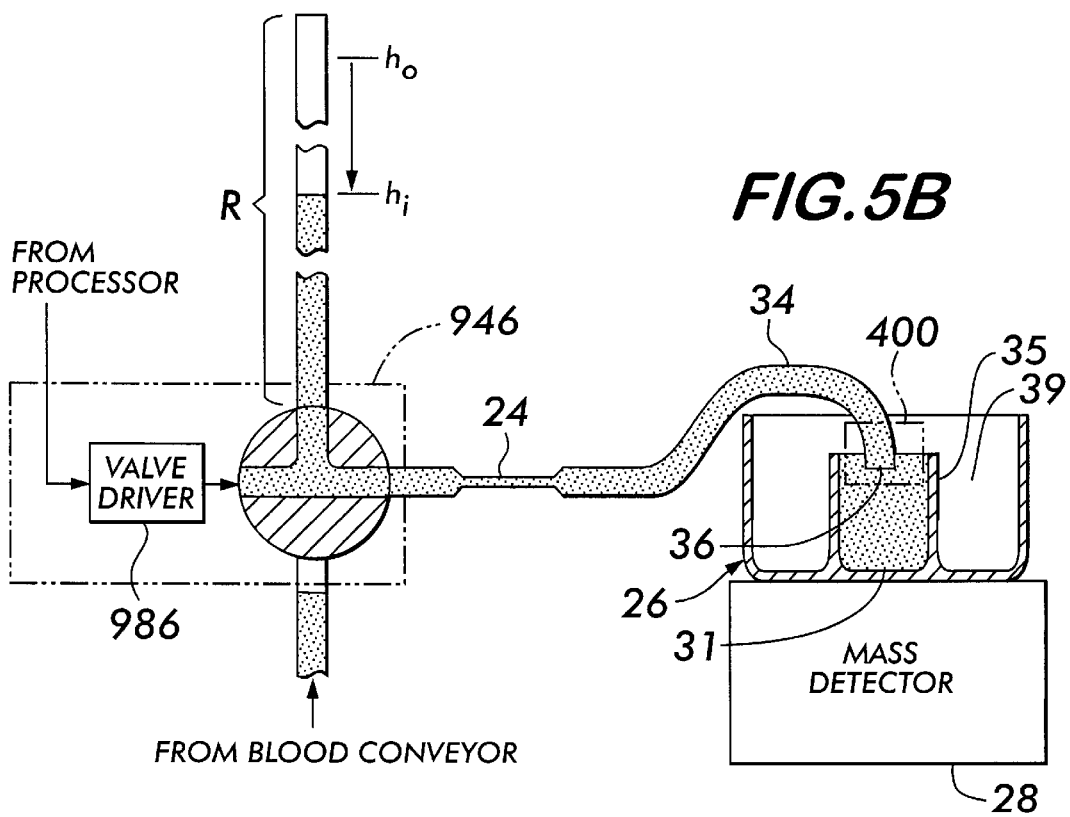
FIG. 5B is a functional diagram of the valve activated to permit the column of blood to fall and be collected in a collector.
Figure 5C:
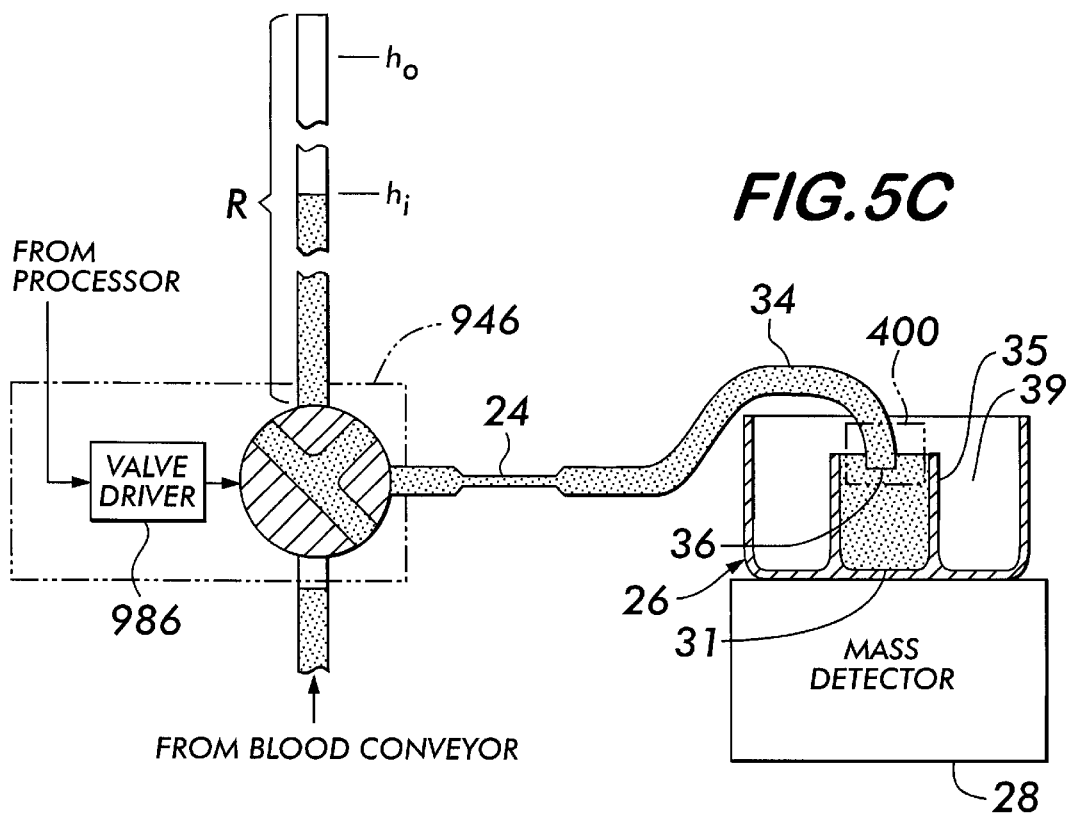
Figure 5D:
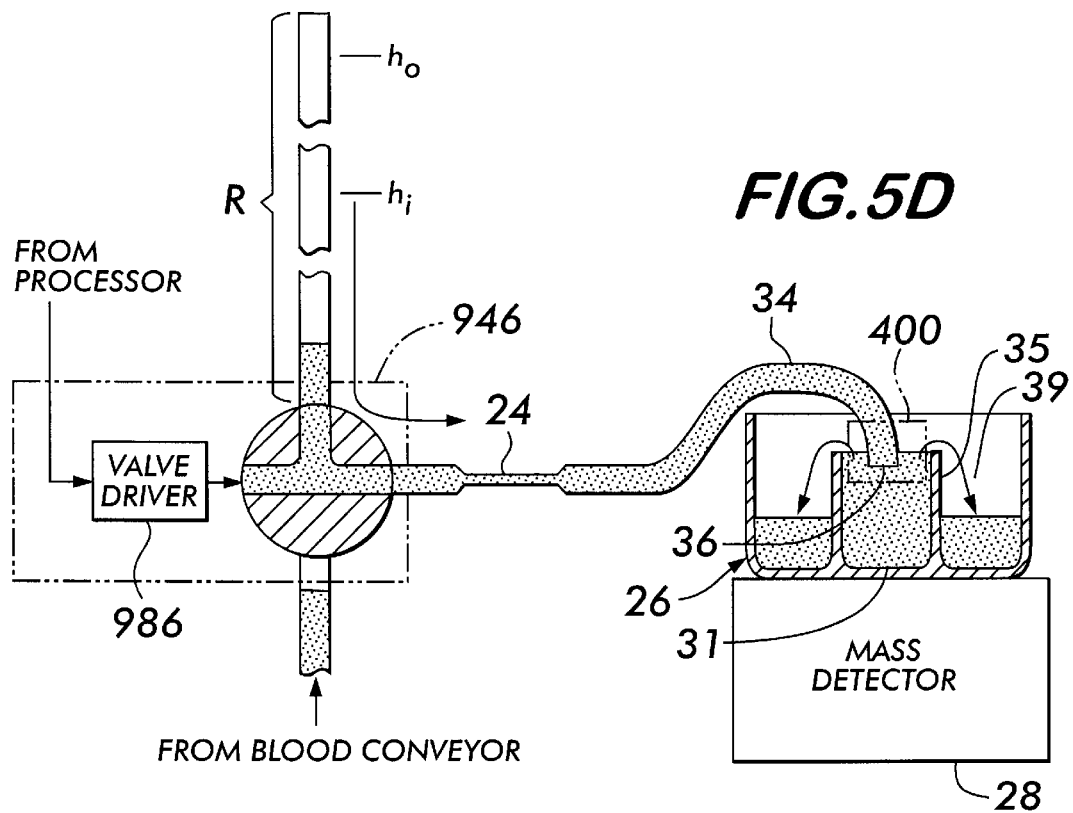

Using this configuration of riser tube R and flow restrictor 24, once the column of blood 38 is generated (as shown in FIG. 4), when the valve mechanism 946 is rotated to the position shown in FIG. 5B, the column of blood 38 is subjected to a decreasing pressure differential that moves the column 38 through a plurality of shear rates (i.e., from a high shear rate at the beginning of the test run to a low shear rate at the end of the test run, as can be clearly seen in the column height change—FIG. 1A and the mass accumulating in the collector 26'—FIG. 1B), which is especially important in determining the viscosity of non-Newtonian fluids, such as blood. In particular, once the desired height, $h_i$ is achieved by the column of blood 38 and with the upper end of the riser tube R exposed to atmospheric pressure, a pressure differential is created between the column of fluid 38 and the outlet 36 of the adaptor 34. As a result, the column of blood 38 flows down the riser tube R, through the flow restrictor 24, through the adaptor 34 and into the collector 26'. As the column of blood 38 flows through these components, the movement of column of blood 38 causes the pressure differential to decrease, thereby causing the movement of the column of blood 38 to slow down. This movement of the column of blood 38, initially at a high shear rate and diminishing to a low shear rate, thus covers the plurality of shear rates. However, it should be understood that it is within the broadest scope of this invention to include any other configurations where the column of blood 38 can be subjected to a decreasing pressure differential in order to move the column of blood 38 through a plurality of shear rates.

The rate of flow through the flow restrictor 24 is equal to the rate of change of the mass of the blood 300 collected on the mass detector 28. Hence, the corresponding flow rate in the flow restrictor 24 can be expressed as:

$$Q(t) = \frac{1}{\rho}\frac{dm}{dt} \quad (1)$$

where $\rho$ is the density of the blood.

In order to determine the viscosity of the blood, it is necessary to know the pressure drop across the flow restrictor 24. What is measured using the MDCBV 20 is the total pressure drop between the riser tube R and the flow restrictor 24 including not only the pressure drop across the flow restrictor or capillary tube 24 ($\Delta P_c$) but also the pressure drop occurring at the inlet and outlet ($\Delta P_e$) of the capillary tube 24. One of the accurate methods for determining ($\Delta P_e$) is to make a Bagley plot (see C. W. Macosko, *Rheology: Principles, Measurements, and Applications* (VCH, 1993)) with at least two short capillary tubes (not shown) of the same diameter. Hence, the pressure drop occurring at the inlet and at the outlet of the capillary tube 24 has to be subtracted from the total pressure difference ($\Delta P_t$). Considering these pressure drops, the pressure drop across the capillary tube 24 can be described as $$\Delta P_c = \Delta P_t - \Delta P_e \quad (2)$$

It should be noted that the contribution from the second term on the right hand side ($\Delta P_e$) in Eq. (2) is less than 0.5%; hence this term can be neglected for all practical purposes, and as a result, equation 2 reduces to:

$$\Delta P_c = \Delta P_t \quad (3)$$

An expression, therefore, for the total pressure as well as the pressure across the capillary tube 24 is:

$$\Delta P_t = \Delta P_c = \rho g[h_i - \Delta h(t) - h_\infty] = \rho g[h_i - h_\infty \Delta h(t)] \quad (4),$$

where $\Delta h(t)$ represents the changing height of the falling column of blood 38 and is given by the following equation:

$$\Delta h(t) = \frac{4m(t)}{\rho \pi \phi_R^2} \quad (5)$$

and where:

$h_i$ is the initial height of the column of blood 38;

$h_\infty$ is the final height of the column of blood 38 after a long period of time; and m(t) is the mass of the collector 26 over time.

In addition, the final mass after a long period of time, $m_\infty$, can be expressed in terms of the height of the column of blood 38 as follows:

$$m_\infty - m_i = \rho\left(\frac{\pi \phi_R^2}{4}\right)(h_i - h_\infty); \quad (6)$$

and solving equation 6 for $(h_i - h_\infty)$, $$(h_i - h_\infty) = \frac{4(m_\infty - m_i)}{\rho \pi \phi_R^2} \quad (7)$$

Thus, making the substitution of equations 5 and 7 into equation 4, $$\Delta P_c = \rho g \left[\frac{4(m_\infty - m_i)}{\rho \pi \phi_R^2} - \frac{4m(t)}{\rho \pi \phi_R^2}\right] \quad (8)$$

$$= \frac{4g}{\pi \phi_R^2}[m_\infty - m_i - m(t)]$$

It is assumed that any surface tension effects are constant with time and throughout the test run, e.g., the surface tension experienced at $h_i$ is similar to the surface tension effect experienced at $h_\infty$.

The significance of equation 8 includes, among other things, that in order to determine the pressure across the capillary tube 24, only the final mass, $m_\infty$, the diameter of the riser R and the mass data detected by the mass detector 28, m(t), need be known; the initial height of the blood column 38, $h_i$, nor the final height, $h_\infty$, nor the initial mass, $m_i$, need to be known. Furthermore, equation 8 also represents, in accordance with the assumption that the surface tension is constant, a surface tension-free capillary.

Non-Newtonian Fluids

The shear rate dependent viscosity for a non-Newtonian fluid, such as blood, flowing in the capillary tube 24 is obtained from experimental data with some mathematical treatment, and the necessary equations can be found in any standard handbook (e.g., C. W. Macosko). The shear rate at the capillary tube 24 wall is obtained form the classical Weissenberg-Rabinowitsch equation (see S. L. Kokal, B. Habibi, and B. B. Maini, Novel Capillary Pulse Viscometer for non-Newtonian Fluids, Review of Scientific Instrument, 67(9), pp. 3149–3157 (1996)):

$$\dot{\gamma}_w(t) = -\frac{dV_z}{dr}\bigg|_{r=R} \quad (9)$$

$$= \frac{1}{4}\dot{\gamma}_{aw}\left[3 + \frac{d\ln Q}{d\ln \tau_w}\right]$$

where $\dot{\gamma}_{aw}$ is the apparent or Newtonian shear rate at the wall and where $\phi_c$ is the diameter of the capillary tube 24.

$$\dot{\gamma}_{aw}(t) = \frac{32Q(t)}{\pi \phi_c^3} \quad (10)$$

and the shear stress at the wall is given by:

$$\tau_w(t) = \frac{\Delta P(t)\phi_c}{4L_c} \quad (11)$$

Thus, the viscosity corresponding to the wall shear rate is calculated in the form of a generalized Newtonian viscosity:

$$\eta = \frac{\tau_w}{\dot{\gamma}_w} = \frac{\pi \phi_c^4 \Delta P}{32 Q L_c} \left(3 + \frac{d \ln Q}{d \ln \tau_w}\right)^{-1} \quad (12)$$

$$= \frac{\rho g \phi_c^4}{8 L_c \phi_R^2} \frac{[m_\infty - m_i - m(t)]}{\left(\frac{dm}{dt}\right)\left(3 + \frac{1}{n'}\right)}$$

where $\frac{1}{n'} = \frac{d \ln Q}{d \ln \tau_w}$.

Thus, Equation 12 represents the viscosity of the blood in terms of the mass measured by the MDCBV 920.

The viscosity versus shear rate information can be obtained from equations 9–12 by measuring the mass of the collected fluid with respect to the time from which the pressure drop and flow rate can be calculated. The values of R and $L_c$ must be obtained by calibration. Since equation (9) is non-linear, the procedure to calculate the shear rate and the corresponding viscosity is not straightforward. One of the approaches to obtain the viscosity from the general equations presented above is to adopt a finite difference technique for differentiation of equation (9). If there is enough data near the point of interest, it is possible to evaluate the derivative as:

$$\frac{1}{n'} = \frac{d \ln Q}{d \ln \tau_w} = \frac{1}{n} \quad (13)$$

where n is simply the exponent of the power law constitutive equation. Even though the power-law exponent is used in the above equations, this does not limit the capability of the present measurement for power-law fluids. The rigorous approach can still be taken for obtaining a viscosity versus shear rate relationship for any fluid (see S. L. Kokal, B. Habibi, and B. B. Maini, "Novel Capillary Pulse Viscometer for non-Newtonian fluids, Review of Scientific Instrument, 67(9), 3149–3157 (1996)).

In application Ser. No. 09/789,350 there is a figure, namely, FIG. 7, which illustrates the viscosity results using a mass detector viscometer for blood and which shows an excellent agreement with those from a conventional rotating viscometer, e.g., the Physica UDS-200 over a range of shear rates.

As mentioned earlier FIGS. 1A and 1B provide a summary of the height vs. time characteristic, and the mass vs. time characteristic, of the falling column of blood 38 during the viscosity test run. As can be seen in FIG. 8A, the level of the column of blood 38 initially is at $h_i$. During the test run, the column of blood 38 falls and arrives at a final column height of $h_\infty$ after a long period of time (e.g., 2–5 minutes after the column of blood 38 begins to fall). As also mentioned earlier, this final height $h_\infty$ can be attributed to both the surface tension effect of the gas-liquid interface 23 (FIG. 4) as well as any yield stress, $\tau_y$, exhibited by the blood. With regard to the change in mass, m(t), as shown in FIG. 8B, the mass climbs quickly and then slows down towards a final mass value, $m_\infty$ after a long period of time. As mentioned earlier, what is important here is that the viscosity of the blood can be determined using the MDCBV 920 without the need to know $h_i$ and $h_\infty$.

Figure 9:
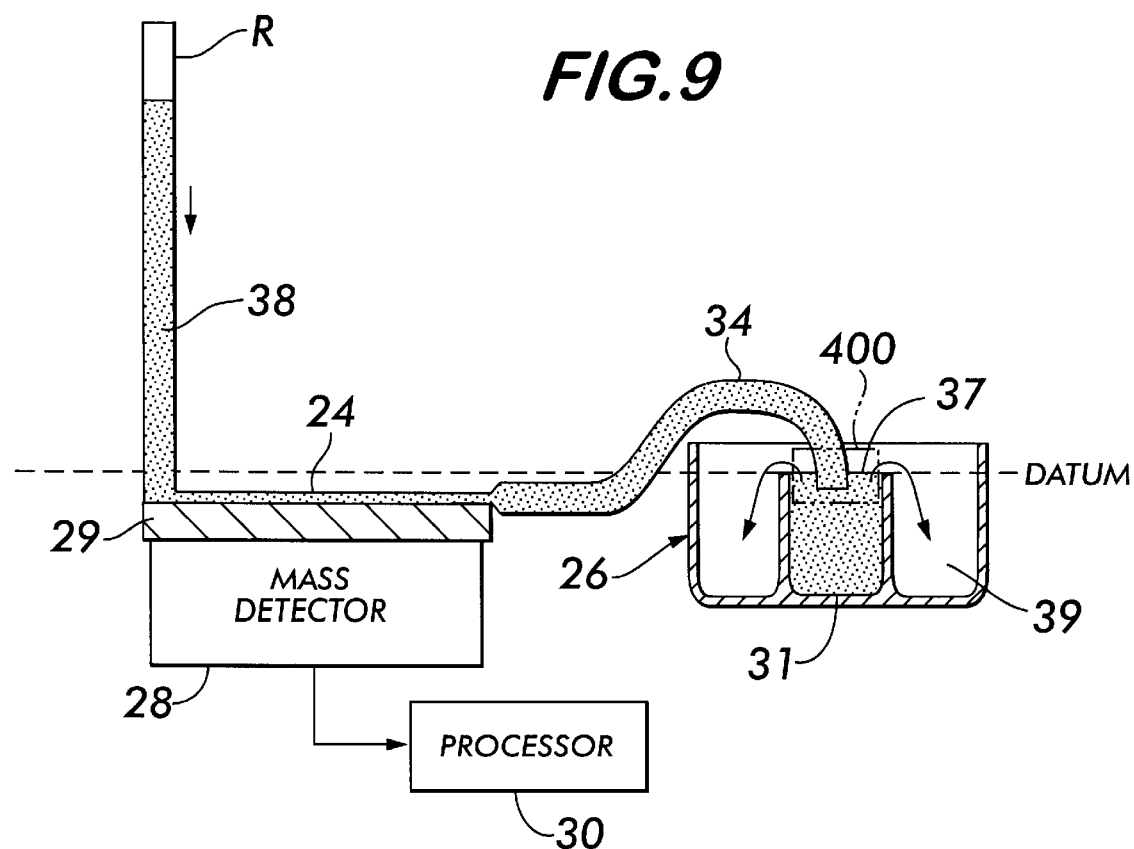
FIG. 9 depicts a fourth embodiment of the MDCBV wherein the changing mass of falling column of blood is detected.
Figure 10:
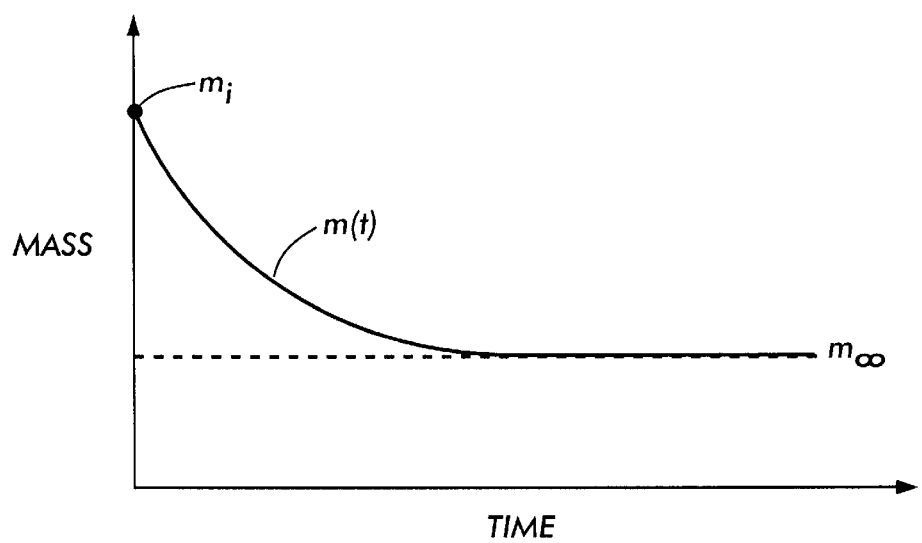
FIG. 10 depicts the mass vs. time plot the falling column of blood for the fourth embodiment of FIG. 9.
Figure 11:
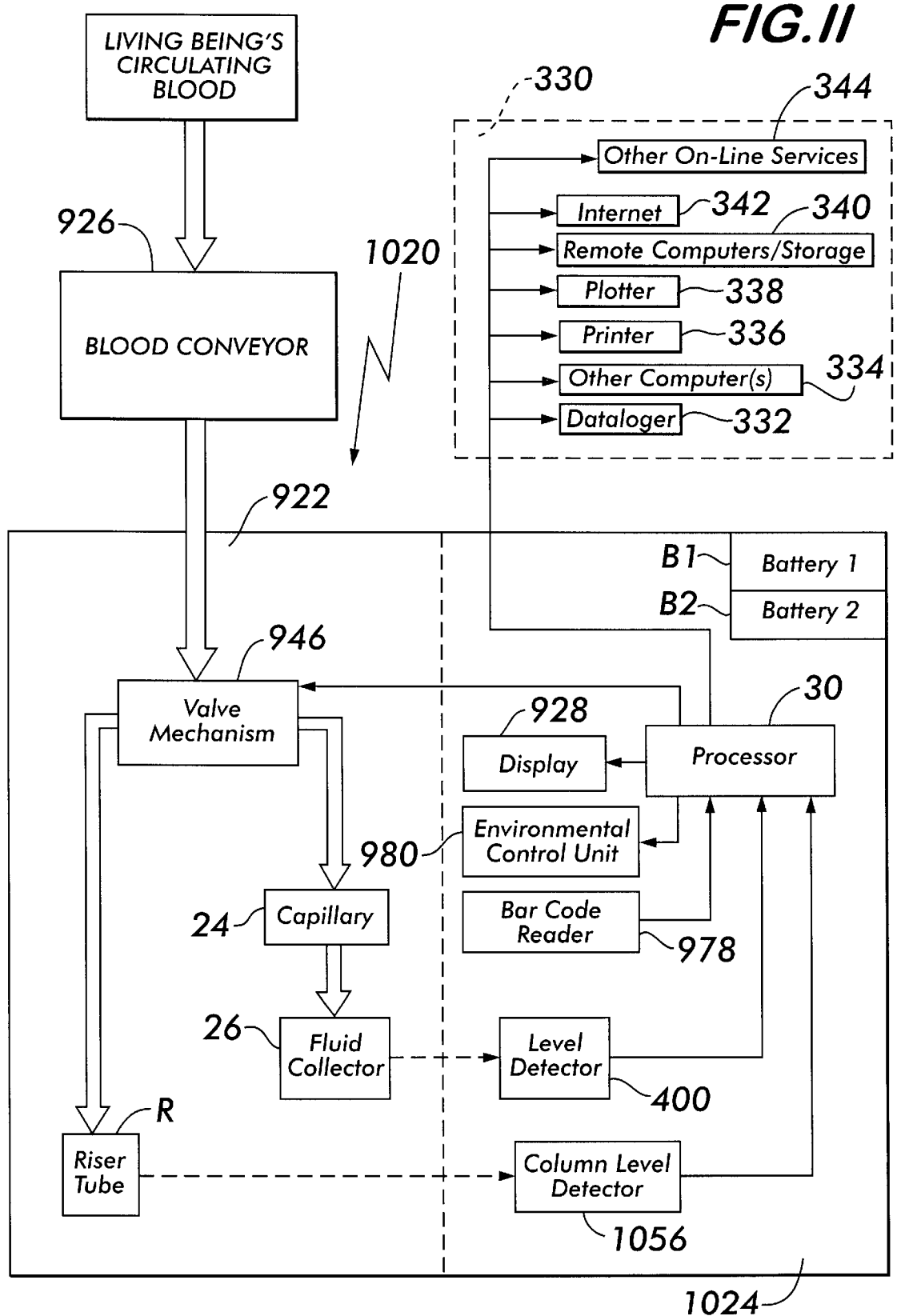
FIG. 11 is a block diagram of a SRSC blood viscometer using a column height detector known as a column height detection capillary (CHDC) blood viscometer wherein the changing height of a falling column of blood is monitored.

FIG. 9 depicts a fourth embodiment of the MDCBV 920 wherein the changing mass of the riser R and flow restrictor 24 are detected, rather than detecting the change in mass of the collected blood 300 in the collector 26. Thus, rather than obtaining an increasing mass with time, the mass detector 28 detects the decreasing mass of the riser R/flow restrictor 24 assembly with time, as shown in FIG. 10. The empty weight of the riser R, flow restrictor 24 and a base 29 (upon which the flow restrictor 24 is disposed) are taken into account before the test run is conducted. As a result, the expression for the pressure drop across the capillary tube 24 is:

$$\Delta P_c = \frac{4g}{\pi \phi_R^2} [(m_i - m_\infty) - m(t)]. \quad (14)$$

Other than that, the theory of operation of this fourth embodiment of the MDCBV 920 is similar to that discussed above with regard to the other embodiments of the MDCBV 920.

A column height detection capillary (CHDC) blood viscometer 1020 is discussed next.

The CHDC blood viscometer 1020 utilizes the same structure, for example, the riser tube R and the flow restrictor 24, but with the mass detector 28 and the overflow detector 981 replaced by column level detector 1056. As a result, the viscosity of the circulating blood of the living being can be determined using the CHDC viscometer 1020. In particular, it can be shown that the viscosity of the circulating blood, $\eta$, is given by:

$$\eta = \frac{\rho g \phi_c^4}{8 L_c \phi_R^2} \left(\frac{h_i - h_\infty - \Delta h(t)}{\frac{d h(t)}{dt}\left(3 + \frac{1}{n'}\right)}\right)$$

Figure 12:
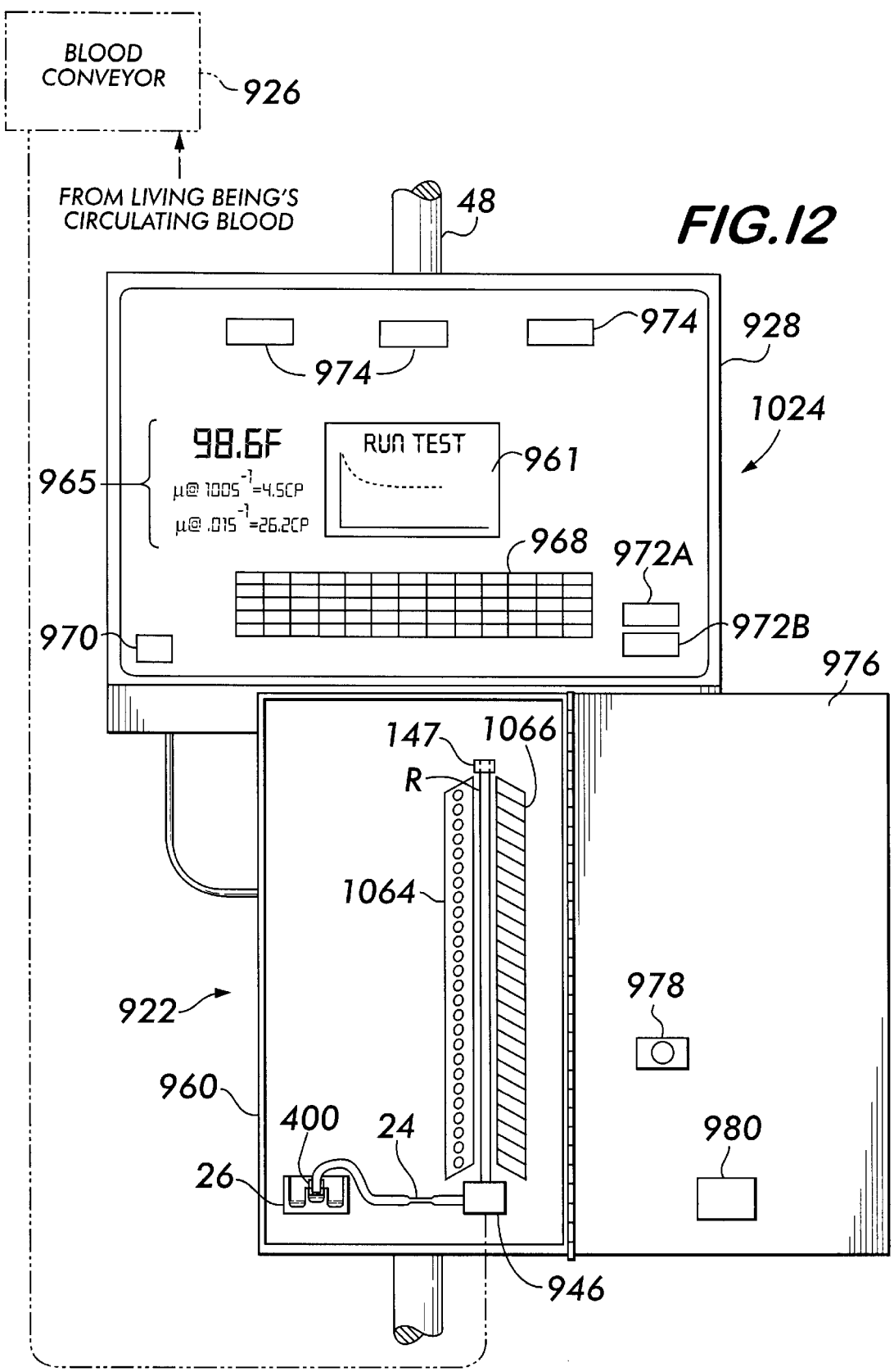
FIG. 12 is a front view of an embodiment of the CHDC blood viscometer.

The column level detector 1056 is similar to the one disclosed in application Ser. No. 09/573,267 whose entire disclosure is incorporated by reference herein. The column level detector 1056 detects the level of the column of blood in the riser tube R and may comprise and LED array 1064 and a CCD 1066 arrangement (FIG. 12). To that end, the CHDC blood viscometer 1020 basically comprises the blood receiver 922 and an analyzer/output portion 1024.

It should be emphasized that it is within the broadest scope of this invention to include all ways known in the art for detecting the level of the column of blood and the present invention is not limited, in any way, to the use of optical detection.

As with the MDCBV 920, the output side 3 of the flow restrictor 24 can be integrally formed with the input side 5 of the adaptor 34.

Figure 13:
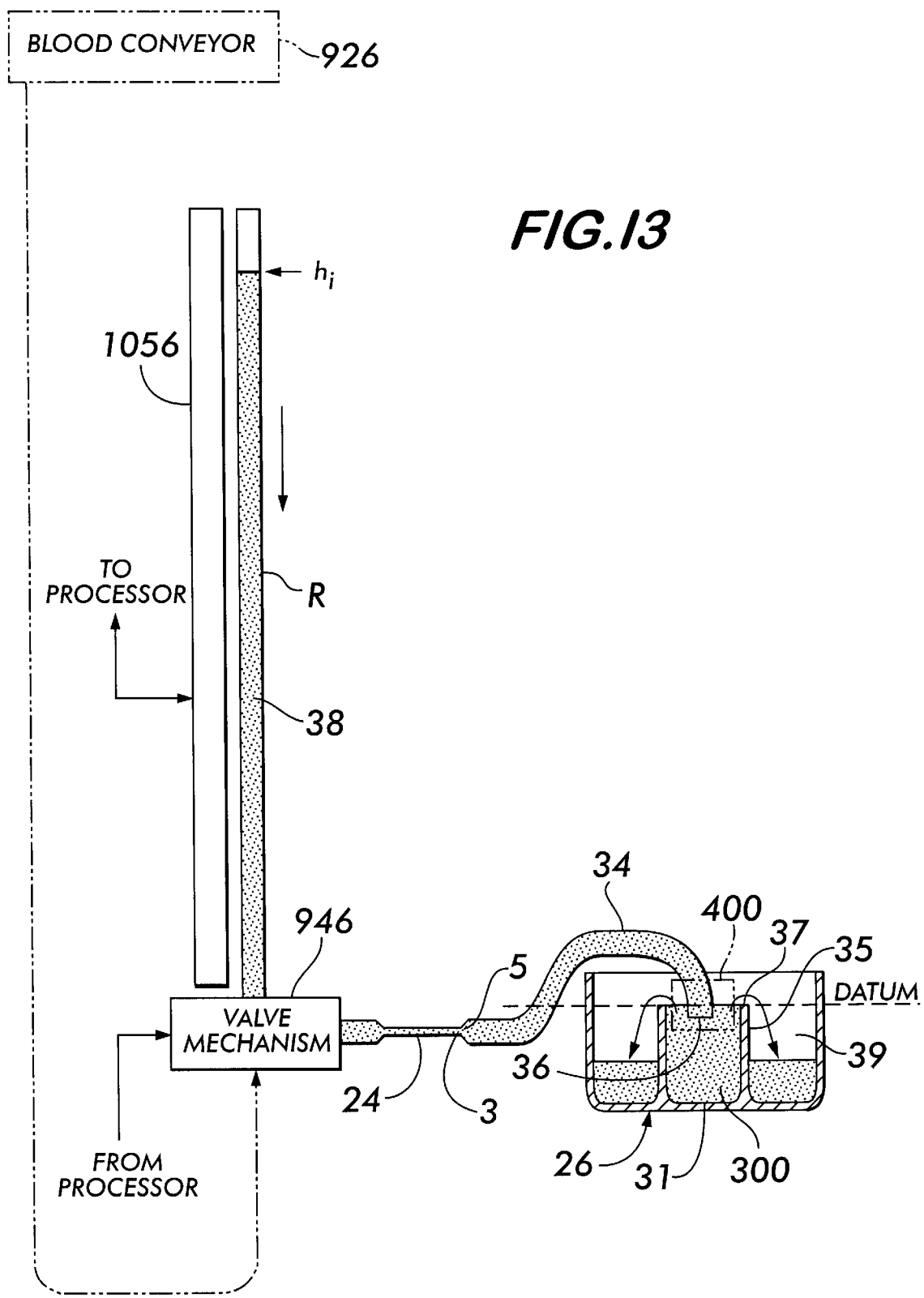
FIG. 13 is a functional diagram of the CHDC blood viscometer.

FIG. 12 depicts one embodiment of the CHDC blood viscometer 1020 which operates similarly to the MDCBV 920 except that the level of the column of blood 38 is monitored rather than the changing mass in the collector 26. In addition, the function of the overflow detector 981 in the MDCBV 920 is accomplished by the column level detector 1056, thereby informing the processor 30 when to operate the valve mechanism 960 to allow the column of blood 38 to fall. As a result, the CHDC blood viscometer 1020 utilizes height vs. time data, as shown in FIG. 1A, to determine the blood viscosity. FIG. 13 is a functional diagram of the CHDC blood viscometer 1020 that depicts the operation of the CHDC blood viscometer 1020, including the use of the submerged end 36 of the adaptor 34 and the level detector 400.

Figure 14:
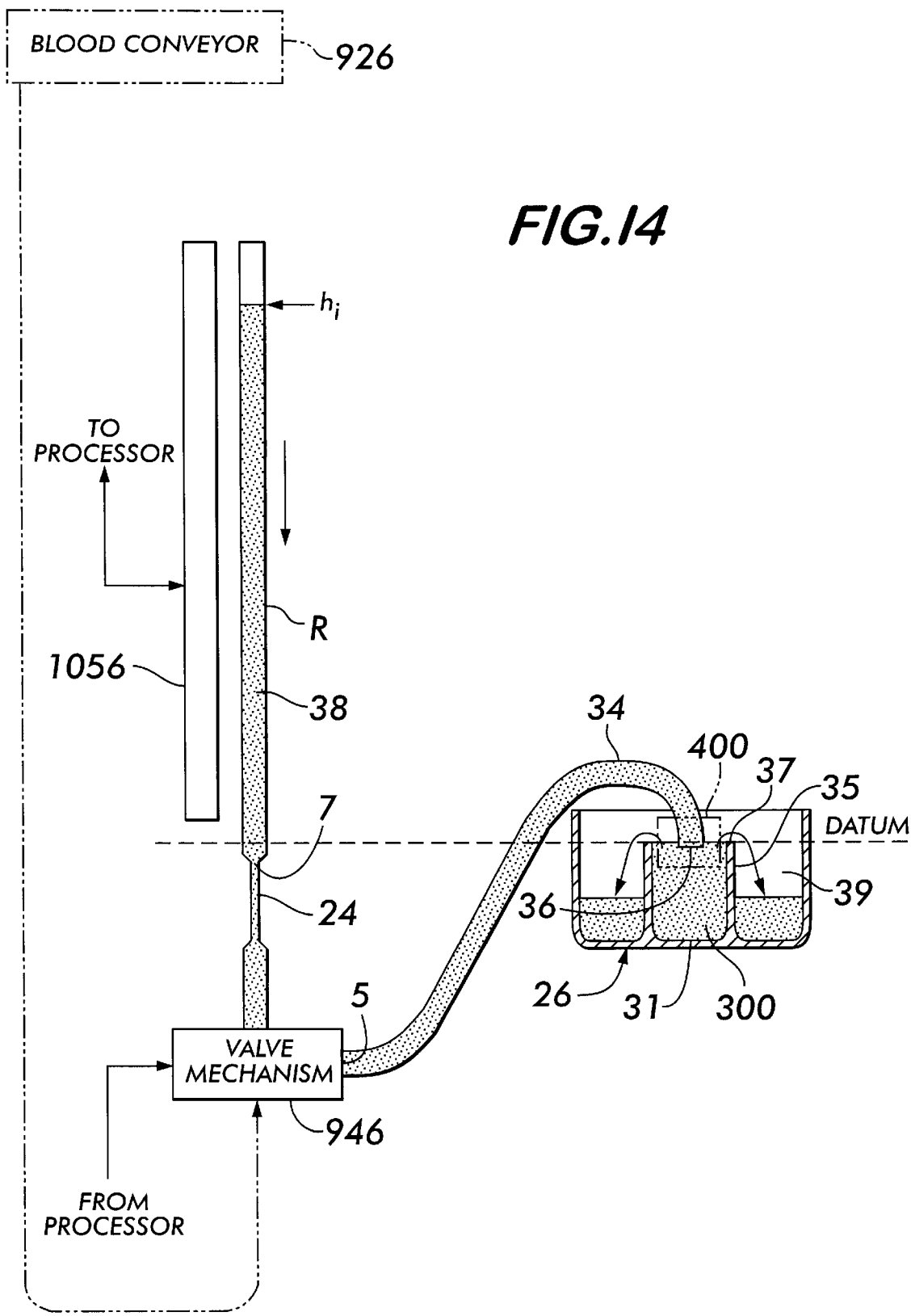
FIG. 14 is a functional diagram of a second embodiment of the CHDC blood viscometer having an alternative location of the flow restrictor.

FIG. 14 is a second embodiment of the CHDC blood viscometer 1020 wherein the flow restrictor 24 forms the lower end of the riser tube R, rather than being located on the other side of the valve mechanism 946. As a result, the input side 5 of the adaptor 34 is coupled to the valve mechanism 946. For proper operation, the datum line needs to be above the input side 7 of the flow restrictor 24, as shown in FIG. 14. Other than that, the operation of this variation is governed by the same equations for the first embodiment of the CHDC blood viscometer 1020 as will be discussed below.

Figure 15:
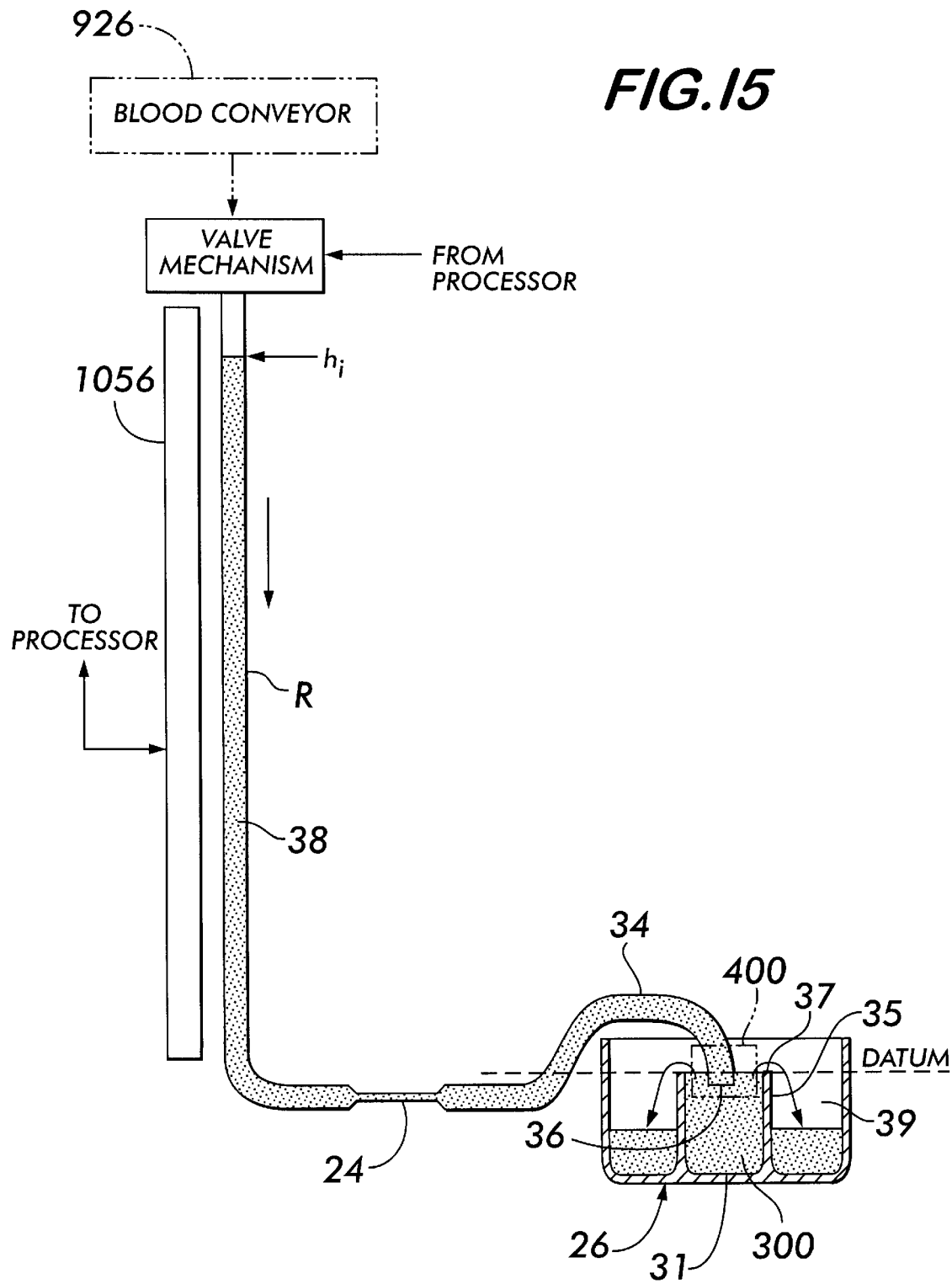
FIG. 15 is a functional diagram of a third embodiment of the CHDC blood viscometer having an alternative location of the valve mechanism.

FIG. 15 depicts a third embodiment of the CHDC blood viscometer 1020 wherein the valve mechanism 946' is positioned at the top of the riser tube R, rather than at the bottom. The same discussion that applies to the third embodiment of the MDCBV 920 that was discussed earlier, applies here for the CHDC blood viscometer 1020.

Without further elaboration, the foregoing will so fully illustrate our invention and others may, by applying current or future knowledge, readily adapt the same for use under various conditions of service.

We claim:

1. An apparatus for determining the viscosity of the circulating blood of a living being over plural shear rates using a decreasing pressure differential, said apparatus comprising:

a lumen being positioned at an angle to a horizontal reference greater than zero degrees, said lumen comprising a first end and a second end, said lumen comprising a first known dimension;

a flow restrictor having an inlet and an outlet, said outlet being arranged to deliver any blood that passes therethrough to a collector, said inlet being coupled to said second end, said flow restrictor including some known dimensions;

a valve coupled to the vascular system of the living being at a first port, said valve comprising a second port coupled to said first end;

a sensor for detecting the movement of the blood over time through said apparatus, said sensor generating data relating to the movement of the blood over time;

a processor, coupled to said valve and said sensor, said processor arranged to operate said valve to create a column of blood in said first lumen and said flow restrictor and to establish a pressure differential between said first end and said outlet, said column of blood moving through said lumen and said flow restrictor at a first shear rate caused by said pressure differential, said movement of said column of blood causing said pressure differential to decrease from said first shear rate for generating said plural shear rates; and wherein said processor calculates the viscosity of the blood based on said data relating to the movement of the column of blood over time, said first known dimension of said lumen and said some known dimensions of said flow restrictor.

2. The apparatus of claim 1 wherein said outlet remains submerged in the blood that is being collected in said collector when said column of blood is moving.

3. The apparatus of claim 2 wherein said sensor detects the changing weight of said collector over time as the blood passes from said outlet into said collector.

4. The apparatus of claim 3 wherein said flow restrictor is a capillary tube and wherein the pressure drop across said capillary tube, $\Delta P_c$, is given by:

$$\Delta P_c = \frac{4g}{\pi \phi_R^2}[m_\infty - m_i - m(t)]$$

where, g is gravitational acceleration;

$\phi_R$ is the diameter of said lumen;

$m_\infty$ is the final weight of said collector after a long period of time;

$m_i$ is the initial weight of said collector before said column of blood starts moving; and m(t) is the changing weight of the collector over time.

5. The apparatus of claim 4 wherein the viscosity, $\eta$, is given by:

$$\eta = \frac{\rho g \phi_c^4}{8 L_c \phi_R^2} \frac{[m_\infty - m_i - m(t)]}{\left(\frac{dm}{dt}\right)\left(3 + \frac{1}{n'}\right)}$$

where, $\rho$ is the density of the blood;

$\phi_c$ is the diameter of said capillary tube;

$L_c$ is the length of said capillary tube; and $$\frac{1}{n'} = \frac{d\ln Q}{d\ln \tau_w},$$

where

Q is the volumetric flow rate through said capillary tube; and $\tau_w$ is $$\frac{\Delta P_c \phi_c}{4 L_c}.$$

6. The apparatus of claim 5 wherein the quantity $$\frac{1}{n'}$$

can be approximated by $$\frac{1}{n}$$

where n is the exponent of a power law constitutive equation.

7. The apparatus of claim 3 wherein said sensor is a precision balance or load cell.

8. The apparatus of claim 3 wherein said collector comprises:

a container having an inner compartment in which said outlet is disposed; and an annular compartment surrounding said inner compartment for forming an overflow chamber.

9. A method for determining the viscosity of the circulating blood of a living being over plural shear rates caused by a decreasing pressure differential, said method comprising the steps of:

(a) providing a lumen having a first end and a second end and positioned at an angle to a horizontal reference greater than zero degrees, said lumen having a first known dimension;

(b) coupling an inlet of a flow restrictor to said second end and arranging an outlet of said flow restrictor to deliver any blood that passes therethrough to a collector, said flow restrictor having some known dimensions;

(c) diverting a portion of the circulating blood into said lumen through said first end to form a column of blood in said lumen and said flow restrictor and to establish a pressure differential between said first end and said outlet;

(c) exposing said first end to atmospheric pressure to cause said column of blood to move through said lumen and said flow restrictor, said movement of said column of blood causing said pressure differential to decrease from said first shear rate for generating said plural shear rates;

(d) providing a sensor for detecting the movement of the column of blood over time as the column of blood moves and passes from said outlet into said collector while maintaining said outlet submerged in blood that has collected in said collector, said sensor generating data regarding said movement; and (e) calculating the viscosity of the blood based on the generated data, said first known dimension and said some known dimensions.

10. The method of claim 9 wherein said step of providing a sensor comprises disposing said collector on a mass detector and obtaining an initial weight of said collector before said column of blood begins moving.

11. The method of claim 10 wherein said mass detector comprises a precision balance or a load cell.

12. The method of claim 10 wherein said flow restrictor is a capillary tube and wherein said step of calculating the viscosity comprises determining the pressure drop across said capillary tube, $\Delta P_c$, according to:

$$\Delta P_c = \frac{4g}{\pi \phi_R^2} [m_\infty - m_i - m(t)]$$

where, g is gravitational acceleration;

$\phi_R$ is the diameter of said lumen;

$m_\infty$ is the final weight of said collector after a long period of time;

$m_i$ is the initial weight of said collector before said column of blood starts moving; and m(t) is the changing weight of the collector over time.

13. The method of claim 12 wherein said step of calculating the viscosity of the blood comprises determining the viscosity, $\eta$, of the blood according to:

$$\eta = \frac{\rho g \phi_c^4}{8 L_c \phi_R^2} \frac{[m_\infty - m_i - m(t)]}{\left(\frac{dm}{dt}\right)\left(3 + \frac{1}{n'}\right)}$$

where, $\rho$ is the density of the blood;

$\phi_c$ is the diameter of said capillary tube;

$L_c$ is the length of said capillary tube; and $$\frac{1}{n'} = \frac{d \ln Q}{d \ln \tau_w},$$

where

Q is the volumetric flow rate through said capillary tube; and $\tau_w$ is $$\frac{\Delta P_c \phi_c}{4 L_c}.$$

14. The method of claim 13 wherein the quantity $$\frac{1}{n'}$$

can be approximated by $$\frac{1}{n}$$

where n is the exponent of a power law constitutive equation.

15. An apparatus for determining the viscosity of the circulating blood of a living being over plural shear rates using a decreasing pressure differential, said apparatus comprising:

a first lumen being positioned at an angle to a horizontal reference greater than zero degrees, said lumen comprising a first end and a second end, said first end being exposed to atmospheric pressure, said lumen comprising a first known dimension;

a flow restrictor having an inlet and an outlet, said inlet coupled to said second end, said flow restrictor including some known dimensions;

a valve coupled to the vascular system of the living being at a first port, said valve comprising a second port coupled to said outlet and a third port coupled to an input of a second lumen arranged to deliver any blood that passes therethrough to a collector through an output of said second lumen;

a sensor for detecting the movement of the blood over time through said apparatus, said sensor generating data relating to the movement of the blood over time;

a processor, coupled to said valve and said sensor, said processor arranged to operate said valve to create a column of blood in said first lumen and said flow restrictor and to establish a pressure differential between said first end and said output, said column of blood moving through said lumen and said flow restrictor at a first shear rate caused by said pressure differential, said movement of said column of blood causing said pressure differential to decrease from said first shear rate for generating said plural shear rates; and wherein said processor calculates the viscosity of the blood based on said data relating to the movement of the column of blood over time, said first known dimension of said first lumen and said some known dimensions of said flow restrictor.

16. The apparatus of claim 15 wherein said inlet of said flow restrictor is positioned at an elevation that is lower than the elevation of said output of said second lumen.

17. The apparatus of claim 16 wherein said outlet remains submerged in the blood that is being collected in said collector when said column of blood is moving.

18. The apparatus of claim 17 wherein said sensor detects the changing weight of said collector over time as the blood passes from said outlet into said collector.

19. The apparatus of claim 18 wherein said flow restrictor is a capillary tube and wherein the pressure drop across said capillary tube, $\Delta P_c$, is given by:

$$\Delta P_c = \frac{4g}{\pi \phi_R^2}[m_\infty - m(t)]$$

where,
- g is gravitational acceleration;
- $\phi_R$ is the diameter of said lumen;
- $m_\infty$ is the final weight of said collector after a long period of time;
- $m_i$ is the initial weight of said collector before said column of blood starts moving; and
- m(t) is the changing weight of the collector over time.

20. The apparatus of claim 19 wherein the viscosity, $\eta$, is given by:

$$\eta = \frac{\rho g \phi_c^4}{8 L_c \phi_R^2} \frac{[m_\infty - m_i - m(t)]}{\left(\frac{dm}{dt}\right)\left(3 + \frac{1}{n'}\right)}$$

where,
- $\rho$ is the density of the blood;
- $\phi_c$ is the diameter of said capillary tube;
- $L_c$ is the length of said capillary tube; and $$\frac{1}{n'} = \frac{d \ln Q}{d \ln \tau_w},$$

where
- Q is the volumetric flow rate through said capillary tube; and
- $\tau_w$ is $$\frac{\Delta P_c \phi_c}{4 L_c}.$$

21. The apparatus of claim 20 wherein the quantity $$\frac{1}{n'}$$

can be approximated by $$\frac{1}{n}$$

where n is the exponent of a power law constitutive equation.

22. The apparatus of claim 18 wherein said sensor is a precision balance or load cell.

23. The apparatus of claim 18 wherein said collector comprises:

- a container having an inner compartment in which said outlet is disposed; and
- an annular compartment surrounding said inner compartment for forming an overflow chamber.

* * * * *